(12) United States Patent
Lehmann et al.

(10) Patent No.: US 8,790,118 B2
(45) Date of Patent: Jul. 29, 2014

(54) INTERACTIVE DENTAL RESTORATIVE NETWORK

(75) Inventors: Maryann Lehmann, Darien, CT (US); Robert A. Ganley, Williamsville, NY (US)

(73) Assignees: Shade Analyzing Technologies, Inc., Darien, CT (US); Ivoclar Vivadent AG, Schaan (LI)

( * ) Notice: Subject to any disclaimer, the term of this patent is extended or adjusted under 35 U.S.C. 154(b) by 588 days.

(21) Appl. No.: 11/513,273

(22) Filed: Aug. 31, 2006

(65) Prior Publication Data

US 2007/0026363 A1 Feb. 1, 2007

(51) Int. Cl.
*A61C 13/00* (2006.01)
*G06F 19/00* (2011.01)

(52) U.S. Cl.
CPC .......... *G06F 19/321* (2013.01); *A61C 13/0004* (2013.01)
USPC ....................................................... 433/223

(58) Field of Classification Search
USPC ......... 433/223, 201.1, 202.1, 203.1; 700/163, 700/118, 97, 98, 105
See application file for complete search history.

(56) References Cited

U.S. PATENT DOCUMENTS

| 3,405,446 A | 10/1968 | Wiener ........................... 433/215 |
| 3,861,044 A | 1/1975 | Swinson, Jr. ....................... 32/17 |
| 3,975,760 A | 8/1976 | Yamanaka et al. ............... 358/41 |
| 3,986,777 A | 10/1976 | Roll ................................ 356/176 |
| 4,016,598 A | 4/1977 | Yamanaka ....................... 358/41 |
| 4,106,056 A | 8/1978 | Nagumo et al. ................. 358/50 |
| 4,110,826 A | 8/1978 | Möllgaard et al. ............. 364/526 |
| 4,247,202 A | 1/1981 | Failes ............................... 364/310 |
| 4,414,635 A | 11/1983 | Gast et al. ....................... 356/526 |
| 4,518,258 A | 5/1985 | Broersma ....................... 364/405 |
| 4,547,074 A | 10/1985 | Hinoda et al. ................. 364/405 |
| 4,575,805 A | 3/1986 | Moermann et al. ........... 364/474 |
| 4,576,576 A | 3/1986 | Spanko ............................ 433/72 |
| 4,591,900 A | 5/1986 | Heeb et al. ....................... 358/44 |
| 4,616,933 A | 10/1986 | Leveque et al. ................ 356/416 |
| 4,623,973 A | 11/1986 | Hoffrichter et al. .......... 364/405 |
| 4,654,794 A | 3/1987 | O'Brien ......................... 364/413 |
| 4,657,399 A | 4/1987 | Hall ................................ 356/421 |
| 4,692,481 A | 9/1987 | Kelly .............................. 523/210 |
| 4,802,850 A | 2/1989 | Boon .............................. 433/26 |

(Continued)

FOREIGN PATENT DOCUMENTS

DE 26 41 740 A1 3/1978
DE 195 34 517 A1 3/1997

(Continued)

OTHER PUBLICATIONS

International Preliminary Report on Patentability, application No. PCT/US2007/076530, dated Oct. 9, 2008.

(Continued)

*Primary Examiner* — Ralph Lewis
(74) *Attorney, Agent, or Firm* — Winston & Strawn LLP

(57) ABSTRACT

The invention relates to a computer-based dental restoration system that include a network server having a database storing digital representations, and a communications network providing access to the network server and facilitating direct communication at least between a dentist and a practitioner. The a computer-based dental restoration system also include one or more computers for accessing digital representations over the communications network and displaying the digital representations in a humanly readable format.

23 Claims, 12 Drawing Sheets

(56) References Cited

U.S. PATENT DOCUMENTS

| | | | | |
|---|---|---|---|---|
| 4,813,000 A | 3/1989 | Wyman et al. | | 364/526 |
| 4,836,674 A | 6/1989 | Lequime et al. | | 356/319 |
| 4,881,811 A | 11/1989 | O'Brien | | 356/323 |
| 4,903,122 A | 2/1990 | Ozaki et al. | | 358/48 |
| 4,919,617 A | 4/1990 | Antons et al. | | 433/26 |
| 4,978,296 A | 12/1990 | Antons et al. | | 433/26 |
| 5,012,431 A | 4/1991 | Stanziola | | 364/526 |
| 5,027,138 A | 6/1991 | Gandrud | | 354/62 |
| 5,055,040 A | 10/1991 | Clar | | 433/26 |
| 5,124,797 A | 6/1992 | Williams et al. | | 358/225 |
| 5,149,267 A | 9/1992 | Longhini et al. | | 433/26 |
| 5,177,694 A | 1/1993 | Graham et al. | | 364/526 |
| 5,231,472 A | 7/1993 | Marcus et al. | | 356/402 |
| 5,240,414 A | 8/1993 | Thompson | | 433/26 |
| 5,261,815 A | 11/1993 | Pozzi | | 433/26 |
| 5,273,429 A | 12/1993 | Rekow et al. | | 433/215 |
| 5,282,025 A | 1/1994 | Sato | | 358/44 |
| 5,313,267 A | 5/1994 | MacFarlane et al. | | 356/405 |
| 5,338,198 A | 8/1994 | Wu et al. | | 433/72 |
| 5,340,309 A | 8/1994 | Robertson | | 433/69 |
| 5,342,194 A | 8/1994 | Feldman | | 433/39 |
| 5,343,267 A | 8/1994 | Kazumi | | 354/410 |
| 5,373,364 A | 12/1994 | Krzyminski | | 356/323 |
| 5,383,020 A | 1/1995 | Vieillefosse | | 356/405 |
| 5,430,811 A | 7/1995 | Fukushima et al. | | 382/254 |
| 5,431,562 A | 7/1995 | Andreiko et al. | | 433/25 |
| 5,434,604 A | 7/1995 | Cleary et al. | | 347/19 |
| 5,440,496 A | 8/1995 | Andersson et al. | | 364/474.05 |
| 5,452,219 A | 9/1995 | Dehoff et al. | | 364/474.05 |
| 5,453,009 A | 9/1995 | Feldman | | 433/215 |
| 5,471,382 A | 11/1995 | Tallman et al. | | 364/406 |
| 5,487,661 A | 1/1996 | Peithman | | 433/29 |
| 5,497,336 A | 3/1996 | Andersson et al. | | 364/474.03 |
| 5,498,157 A | 3/1996 | Hall | | 433/26 |
| 5,515,491 A | 5/1996 | Bates et al. | | 395/155 |
| 5,529,492 A | 6/1996 | Yarovesky et al. | | 433/26 |
| 5,549,476 A | 8/1996 | Stern | | 433/233 |
| 5,575,656 A | 11/1996 | Hajjar | | 433/219 |
| 5,579,393 A | 11/1996 | Conner et al. | | 380/25 |
| 5,587,912 A | 12/1996 | Andersson et al. | | 433/215 |
| 5,616,899 A | 4/1997 | Recigno | | 235/375 |
| 5,624,262 A | 4/1997 | Yarovesky et al. | | 433/223 |
| 5,685,712 A | 11/1997 | Fischer | | 433/26 |
| 5,690,486 A | 11/1997 | Zigelbaum | | 433/29 |
| 5,692,900 A | 12/1997 | Fischer | | 433/26 |
| 5,725,372 A | 3/1998 | Leon | | 433/26 |
| 5,733,126 A | 3/1998 | Andersson et al. | | 433/233 |
| 5,745,229 A | 4/1998 | Jung et al. | | 356/73 |
| 5,759,030 A | 6/1998 | Jung et al. | | 433/29 |
| 5,766,006 A | 6/1998 | Murljacic | | |
| 5,798,839 A | 8/1998 | Berner et al. | | 356/402 |
| 5,823,778 A | 10/1998 | Schmitt et al. | | 433/214 |
| 5,827,180 A | 10/1998 | Goodman | | 600/300 |
| 5,851,113 A | 12/1998 | Jung et al. | | 433/28 |
| 5,851,115 A | 12/1998 | Carlsson et al. | | 433/215 |
| 5,870,172 A * | 2/1999 | Blume | | 355/27 |
| 5,871,351 A | 2/1999 | Jung et al. | | 433/29 |
| 5,880,826 A | 3/1999 | Jung et al. | | 356/73 |
| 5,899,998 A | 5/1999 | McGauley et al. | | 707/104 |
| 5,930,759 A | 7/1999 | Moore et al. | | 705/2 |
| 5,938,446 A * | 8/1999 | Andersson et al. | | 433/223 |
| 5,960,403 A | 9/1999 | Brown | | 705/2 |
| 5,961,324 A | 10/1999 | Lehmann | | 433/26 |
| 5,966,205 A | 10/1999 | Jung et al. | | 356/71 |
| 5,993,214 A | 11/1999 | Persson | | 433/223 |
| 5,995,138 A | 11/1999 | Beer et al. | | 348/96 |
| 6,008,905 A | 12/1999 | Breton et al. | | 356/402 |
| 6,030,209 A | 2/2000 | Panzera | | 433/26 |
| 6,032,119 A | 2/2000 | Brown et al. | | 705/2 |
| 6,038,024 A | 3/2000 | Berner | | 356/326 |
| 6,047,259 A | 4/2000 | Campbell et al. | | 705/3 |
| 6,049,743 A | 4/2000 | Baba | | 700/163 |
| 6,058,357 A | 5/2000 | Granger | | 702/104 |
| 6,093,019 A | 7/2000 | Morandi et al. | | 433/29 |
| 6,111,650 A | 8/2000 | Rawicz et al. | | 56/402 |
| 6,132,210 A | 10/2000 | Lehmann | | 433/26 |
| 6,190,170 B1 | 2/2001 | Morris et al. | | 433/215 |
| 6,217,334 B1 | 4/2001 | Hultgren | | 433/215 |
| 6,227,850 B1 | 5/2001 | Chishti et al. | | 433/24 |
| 6,244,863 B1 | 6/2001 | Rawicz et al. | | 433/26 |
| 6,254,385 B1 | 7/2001 | Jung et al. | | 433/26 |
| 6,271,913 B1 | 8/2001 | Jung et al. | | 356/73 |
| 6,305,933 B1 | 10/2001 | Lehmann | | 433/26 |
| 6,318,994 B1 | 11/2001 | Chishti et al. | | 433/24 |
| 6,331,113 B1 | 12/2001 | Morris et al. | | 433/215 |
| 6,358,047 B2 | 3/2002 | Lehmann | | 433/26 |
| 6,384,917 B1 | 5/2002 | Fradkin | | 356/402 |
| 6,434,332 B1 | 8/2002 | Kindaichi | | 396/123 |
| 6,450,807 B1 | 9/2002 | Chishti et al. | | 433/24 |
| 6,463,351 B1 | 10/2002 | Clynch | | 700/163 |
| 6,523,009 B1 * | 2/2003 | Wilkins | | 705/3 |
| 6,561,800 B2 | 5/2003 | Lehmann | | 433/26 |
| 6,575,751 B1 * | 6/2003 | Lehmann et al. | | 433/223 |
| 6,764,306 B1 | 7/2004 | DiMarino et al. | | 433/77 |
| 6,786,726 B2 * | 9/2004 | Lehmann et al. | | 433/223 |
| 6,793,489 B2 | 9/2004 | Morris et al. | | 433/26 |
| 6,821,123 B2 * | 11/2004 | Andersson et al. | | 433/215 |
| 6,832,913 B2 | 12/2004 | Lehmann | | 433/26 |
| 6,835,066 B2 * | 12/2004 | Iiyama et al. | | 433/223 |
| 7,393,209 B2 | 7/2008 | Lehmann | | 433/26 |
| 7,474,307 B2 | 1/2009 | Chishti et al. | | 345/418 |
| 7,682,150 B2 | 3/2010 | Jung et al. | | 433/26 |
| 7,694,129 B2 | 4/2010 | DiRienzo | | 713/153 |
| 7,905,725 B2 | 3/2011 | Chishti et al. | | 433/24 |
| 8,105,084 B2 | 1/2012 | Lehmann et al. | | 433/223 |
| 8,145,340 B2 | 3/2012 | Taub et al. | | 700/117 |
| 2002/0004725 A1 | 1/2002 | Martin et al. | | 705/2 |
| 2003/0148243 A1 | 8/2003 | Kerschbaumer et al. | | 433/29 |
| 2006/0010007 A1 | 1/2006 | Denman et al. | | 705/2 |
| 2006/0177795 A1 | 8/2006 | Sorensen et al. | | 433/98 |
| 2007/0244581 A1 | 10/2007 | Nyholm | | 700/83 |

FOREIGN PATENT DOCUMENTS

| | | |
|---|---|---|
| EP | 0 360 657 A1 | 3/1990 |
| EP | 1 486 900 A1 | 12/2004 |
| JP | 64-052455 A | 2/1989 |
| JP | 01052454 | 2/1989 |
| JP | 04301530 A | 10/1992 |
| JP | 04338465 A | 11/1992 |
| JP | 9034963 | 2/1997 |
| JP | 11128248 A | 5/1999 |
| JP | 2002528832 | 9/2002 |
| JP | 2006021024 | 1/2006 |
| WO | WO 86/03292 A1 | 6/1986 |
| WO | WO 91/02955 A1 | 3/1991 |
| WO | WO 95/15731 A1 | 6/1995 |
| WO | WO 97/01308 A1 | 1/1997 |
| WO | WO 97/24075 A1 | 7/1997 |
| WO | WO 98/32394 A1 | 7/1998 |
| WO | WO 98/44865 A1 | 10/1998 |
| WO | WO 00/25696 A1 | 5/2000 |
| WO | WO 2004/080324 A1 | 9/2004 |
| WO | WO 2005/098727 A2 | 10/2005 |
| WO | WO 2006/037862 A1 | 4/2006 |

OTHER PUBLICATIONS

Berland, "Cosmetic Practice Building," Dental Products Report, Feb. 1998.

Berland, "Show Your Stuff! Building a Referral Practice Through Computer Imaging and Cosmetic Dentistry," Contemporary Esthetics and Restoration Practice, Jul./Aug. 1998, pp. 50-57.

Engelhardt, "Practice Builders: Computer Imaging," Contemporary Esthetics and Restoration Practice, Jul./Aug. 1998, pp. 58-59.

Pfefferkorn et al., "The Integrated Computer Network. The Computer Network of the Center for Tooth-Color Matching and Computer-Assisted Restorations," Schweiz Monatsschr Zahnmed. 1994; 104(8):962-71. (Original in German, English translation provided.).

Touati, "Improved Communication Benefits Provided by Intraoral Camera Systems", Pract Periodontics Aesthet Dent. Nov.-Dec. 1998; 10(9):1244, 1246.

Internet Search for "Prosthodontics"—Jun. 2001.

(56) References Cited

OTHER PUBLICATIONS

International Search Report and Written Opinion dated Mar. 13, 2008 from application No. PCT/US2007/076530.
Vaughan et al., "A Client/Server Approach to Telemedicine", (1995) <http://www.ncbi.nlm.nih.gov/pmc/articles/PMC2579199/pdf/procascamc00009-0805.

Yamany et al., "A System for Human Jaw Modeling Using Intra-Oral Images", (1998)<http://citeseerx.ist.psu.edu/viewdoc/summary?doi=10.1.1.33.572.

Hou., "Use of computers in private dental practice in Australia", (1991) <http://ses.library.usyd.edu.au/bitstream/2123/4898/1/07.

* cited by examiner

INTERACTIVE DENTAL RESTORATIVE NETWORK

TECHNICAL FIELD

The invention is directed to methods, systems and devices for dental restoration wherein communication between the dentist and restoration laboratory are held in real time to discuss, finalize and optimize a treatment plan for a patient. More specifically, the invention is directed to an interactive computer-based system and method to enable the dentist and restoration laboratory to analyze color images of one or more teeth and teeth preparation so that a replacement tooth or crown can be particularly designed to precisely match the tooth that is to be replaced in certain clinical or cosmetic procedures.

BACKGROUND OF THE INVENTION

Restorative dentistry is the art and science of replacing or restoring lost tooth structure. The amount of tooth structure to be replaced determines what path the operator takes—whether the restoration will be a crown, bridge, inlay, onlay or direct restoration (i.e., a filling). The choice of that path in the past was more simple, due to the limited number of materials and techniques available. For example, U.S. Pat. Nos. 5,766,006 and 5,961,324 describe methods and systems for determining tooth color information based upon digital images provided by a camera and then matching the color of the restoration article (i.e., dental prosthesis) with the determined tooth color. In recent years, however, with the advent of new materials and concepts, treatment choices have expanded in a phenomenal way. Dentists are now facing an overload of information in trying to decide which materials and procedures are the best suited for their particular cases. What the state-of-the-art practitioner needs is a source to be able to go to, at a moment's notice, that will be able to aid him and his lab if necessary in treatment planning and delivering the best restorative dentistry possible, utilizing the most appropriate materials available today. The present invention now satisfies this need.

SUMMARY OF THE INVENTION

The invention relates to a computer-based dental restoration system between a dentist and a practitioner. The system includes a network server having a database for storing digital representations, and a communications network providing access to the network server and facilitating direct communication at least between a dentist and a practitioner. The system further includes one or more computers for accessing digital representations over the communications network and displaying the digital representations in a humanly readable format. Preferably, the practitioner includes one or more of a dentist, a dental specialist, and a dental restoration manufacturer.

Generally, the digital representations includes one or more of a patient's dental record or aspects thereof, an x-ray of a patient's tooth, a digital image of a patient's tooth, a video image of a patient's tooth, or a preliminary dental treatment plan. The digital representations further include a digital impression which is a three dimensional model of a treatment area. An intraoral scanner is a preferred method for forming this three dimensional model, but other means, such as, scanning of a dental cast can also be used to obtain a digital impression. The digital impression generally is operated on by an application running on at least one of the one or more computers to provide a particular functionality for the dentist or practitioner.

Advantageously, the one or more computers include a client application that provides access to the database. The client application generally includes a Web browser. At least one of the one or more computers, the server, or both include a loading application that loads the digital representations into the database and another application that provides access to the database via e-mail.

In the preferred embodiment, the one or more computers provide the dentist and practitioner simultaneous access to at least one of the digital representations, and in a further embodiment, simultaneously perform direct communication. The computer is a desktop or laptop device, a PDA or Blackberry device or a cellular telephone and the communications network includes the Internet.

In another preferred embodiment, the computer-based dental restoration system provides real-time access to the network server and the database further includes information about materials, procedures, preparations concerning dental restoration prostheses. In this embodiment, the communications network transfers voice, video, and data between a dentist and practitioner. Preferably, the communications network is configured to enable the dentist to communicate a prostheses specification, consult with the practitioner, obtain cost and viability options for presentation to a patient, and place an order with the practitioner, wherein elapsed time for the whole process is less than four hours. More preferably, the elapsed time is less than one hour.

BRIEF DESCRIPTION OF THE DRAWINGS

These and other aspects of the invention should be more apparent from the following detailed description and drawings in which.

DETAILED DESCRIPTION OF THE INVENTION

Figure 1:
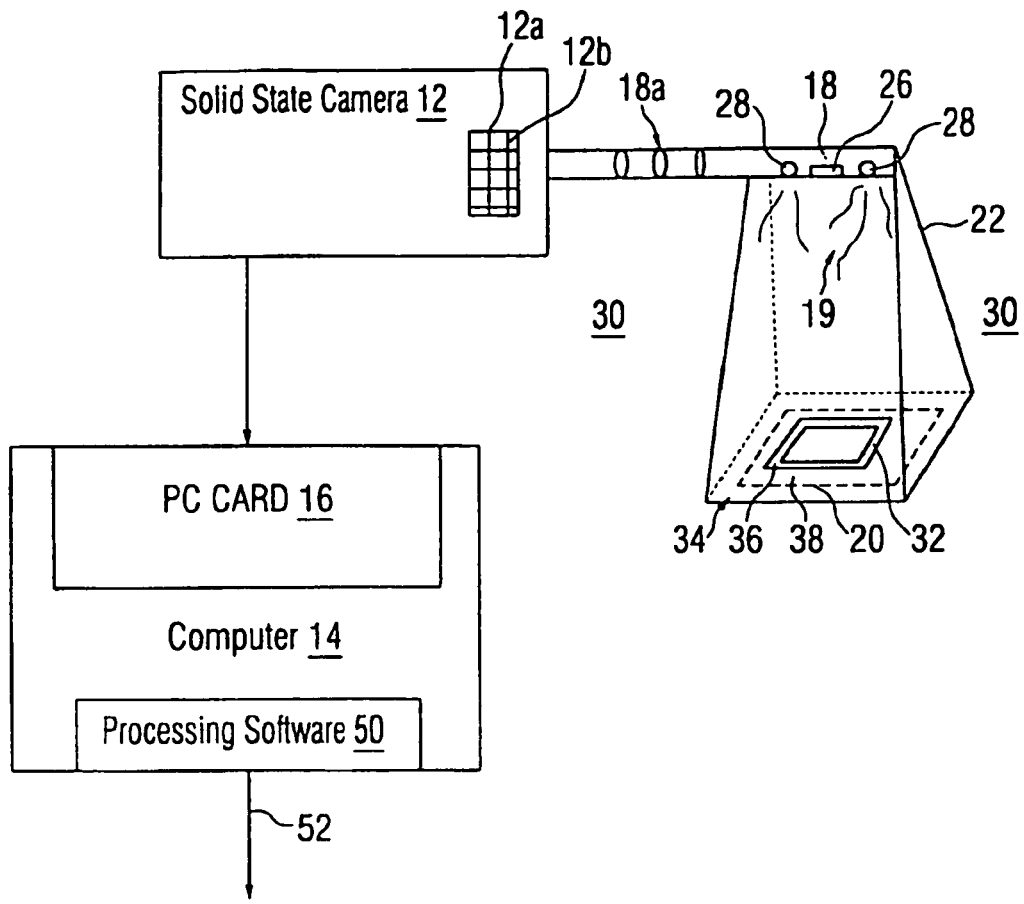
FIG. 1 illustrates a shade analyzer system for capturing images in accord with a specific embodiment of this invention.

The invention relates to an interactive dental restoration method between a dentist and a dental restoration laboratory. The basic steps of this method include identifying a dental restoration need in a patient; designing a preliminary treatment plan that includes design criteria for preparation of a dental prosthesis to be placed in the patient to satisfy the dental restoration need; transmitting the preliminary treatment plan via a communications network to a dental restoration laboratory; and communicating a final treatment plan, including modifications to the preliminary treatment plan where necessary, to the dentist. Typically, the final treatment plan includes information about materials for preparing a dental prosthesis that satisfies the design criteria, and the dental prosthesis is then prepared for placement in the patient. This method enables optimization of the dental restoration with significant savings in time and effort for the dentist, dental technician and the patient.

Generally, the dentist prepares the preliminary treatment plan and the design criteria include digital image representations of the dental restoration need. Thereafter, the preliminary treatment plan can be forwarded to and evaluated by the laboratory before a final treatment plan is formulated and communicated to the dentist. The step of transmitting and evaluating the plan are codirected over the communications network. Thus, the final treatment plan is not implemented in the patient until after interim preparation information is transmitted to the laboratory and confirmed, thus avoiding rework or revision after the plan has been implemented.

Advantageously, the design criteria or the modifications thereto include proposed decay excavation, tooth preparation, or dental prosthesis color. When a dental prosthesis such as a crown, bridge or replacement tooth is needed, the method includes verifying that the dental prosthesis is prepared according to the final treatment plan prior to placement of the dental prosthesis in the patient. In order to obtain the best color match of the dental prosthesis with the patient's teeth, the digital image representations include REAL IMAGE and REFERENCE IMAGES and the modifications include correlation of a color selection for the dental prosthesis to match the REAL IMAGE. Furthermore, the design criteria can include tooth preparation and proposed decay excavation, and the method further comprises a communication of a confirmation or modification, from the laboratory, of the acceptability of one or more of the proposed design criteria.

The invention also relates to a computer-based dental restoration system comprising a network server having a database storing information about materials, procedures and preparations concerning dental restoration prosthesis; a communications network providing access to the network server; and one or more computers at a dental office accessing information stored at the database over the communications network and displaying the information in a humanly readable format. Preferably, the communications network is the Internet, and the information stored in the database comprises preparation diagrams, reduction dimensions, margin design and burs for specific dental restoration prostheses.

Advantageously, the database further stores information concerning one or more patients having dental restoration needs. Also, the network server further comprises application programs for enabling users to query the database regarding specific materials or procedures concerning dental restoration prostheses for confirmation, verification, modification or evaluation of the same, with the one or more computers at the dental office receiving answers from the database to such queries. If desired, a printer located at the dental office can be used to print these answers for use by the dentist in carrying out the treatment plan.

The dental restoration laboratory also includes at least one computer that has access to the network server and the computer(s) at the dental office over the communications network. Preferably, the system includes a digital camera for taking digital images of the patient's teeth that are in need of dental restoration and a communication link for transmitting the digital images to the computer(s) at the dental office. Also, the computer(s) at the dental office store these digital images and the communications network forwards the digital images to the database for storage therein.

The present invention further provides an enhanced dental restoration network as a service for dentists. This network would be established via a computerized link between the dentist, the lab, and, optionally, the lab's databank of the most current information regarding materials, procedures, and other services such as preparation design and surveying for dental restoration prostheses such as caps, crowns, bridges, fillings and the like.

In a typical case, initial steps of complete examination and diagnosis of the patient's dental condition is by the dentist. This generally includes a basic periodontal examination, clinical exam, radiographs, screening for TMD, etc. The dentist also creates a preliminary treatment plan for addressing the dental needs of the patient. When tooth capping or replacement is required, clinical pictures which can are taken and captured on a program and are forwarded to the lab. Theses pictures can be of the color of the patient's teeth, the preparation of a tooth for further treatment, or even of a temporary treatment which can be modified or enhanced before being finalized. The pictures can be taken in any one of a number of ways, as described in more detail below.

In this invention, an on-site advanced restorative system is provided where the dentist takes one or more digital images of the tooth prior to restoration, eliminates areas of decay in the image, and matches the shade of material to be used to restore the tooth based upon the digital images of the tooth prior to removal. In another aspect, the dentist takes digital images of the tooth after preparation and matches the shade of the material to be used in restoration based upon the remaining parts of the tooth. These pictures can be forwarded by facsimile, direct computer link, or by e-mail to the lab for evaluation, along with the dentist's preliminary treatment plan.

Figure 16:
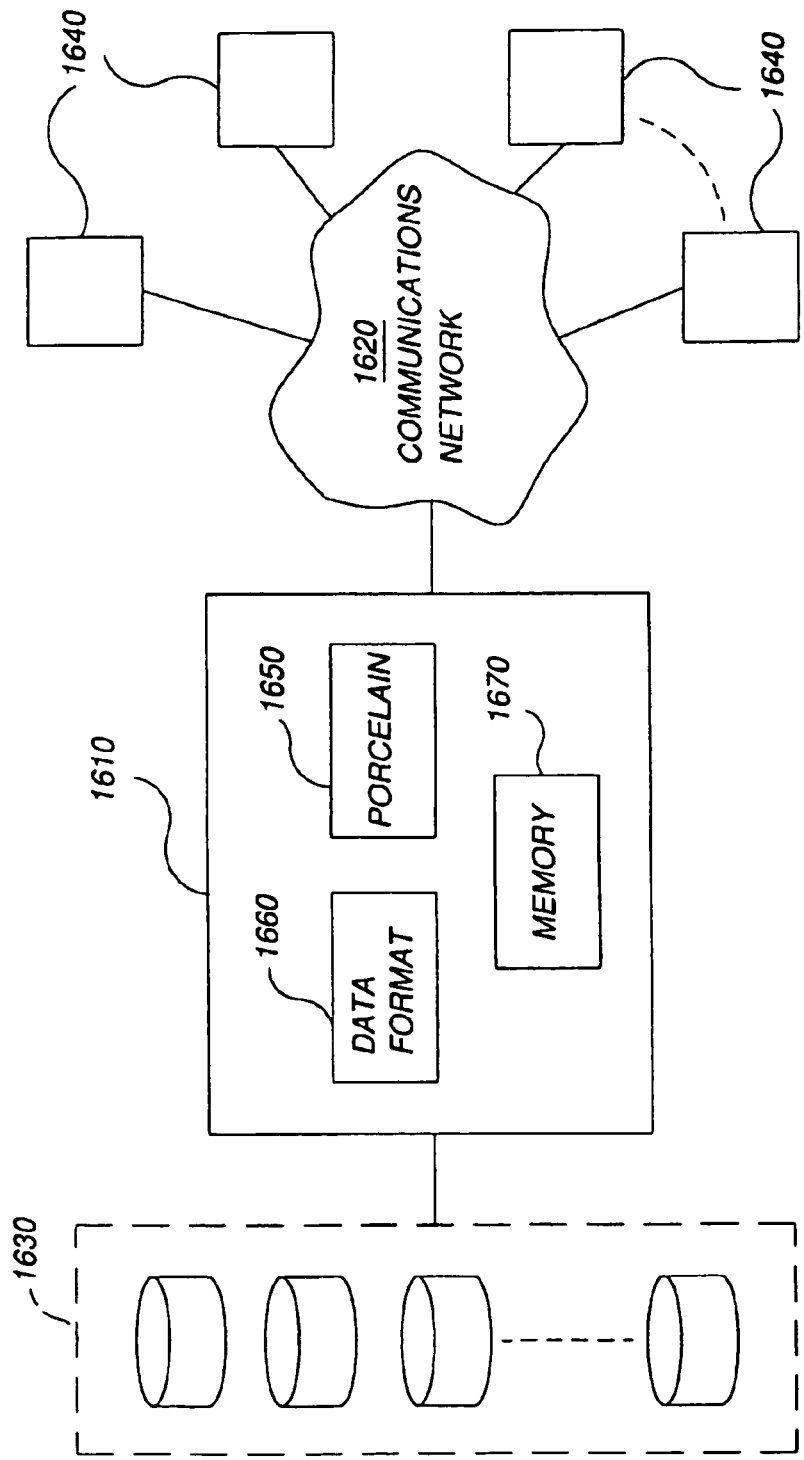
FIG. 16 is a block-diagram of the configuration of the interactive network system of the invention.

After preliminary treatment plans are designed, and areas such as periodontal needs, decay excavation, endodontic concerns are addressed, the restorative needs are considered. If the treatment plan may include fixed prosthodontics (crowns and bridges), the clinical pictures are then forwarded to the lab. The doctor and technician assess the case together prior to accessing the interactive dental restorative network ("the site"). An illustration of such a network is shown in FIG. 16 and described in more detail below. If the case involves only direct restorations, the dentist can go directly to the site.

If the dentist does not have access to the site but his lab does, the doctor could send pictures to the lab, the technician in turn could access the site, and consult back to the doctor giving restorative options as given by the site. This service would be rendered by the labs for dentists that are not comfortable or familiar enough with computers to do their own electronic processing and communication with the site.

The site would provide access for users to obtain information on materials, procedures involved in using such materials such as preparation design, recommended burs to achieve such a preparation, recommended temporization materials, cements that should be used with that given material, instructions on how to use such a cement (i.e., conditions such as whether one should etch or prime, for how long, whether to dry it or not, to pre-cure it or not, etc.), and where to buy such materials. Alternatively, the lab could explain how it would provide such a service or who the dentist could contact to obtain such service. Beyond this, once the treatment is underway, the dentist could verify his preparation with the technician, if necessary, by sending digital images electronically for review prior to final impressions. For a more precise evaluation of the case in treatment, the dentist would scan his preparations and go to the part of the site that would survey the teeth and assess reduction amount. This would typically be used in larger and more complex cases.

The site would offer a number of features for communicating dental restoration data to the dentist and technician. One of the most unique features of the site is that it is interactive. Rather than just being a databank of information for the dentist to review, the dentist would be led through a step by step procedure to determine the most appropriate restorative path to take. The site could be visited periodically to consider alternative procedures, different options or to just confirm that the previous recommendations are clear and are being followed. Although many dentists read articles and reports, and attend seminars to obtain the latest information, until there is a case in hand, a lot of that information is not applicable. By the time a given case corresponds to a case presented at a previous seminar, the dentist may have already forgotten the information. The present method and system provides immediate feedback of the most up-to-date information in real time for the specific need of the current patient.

As the dentist accesses the site, he can immediately be asked certain questions regarding the patient's history. Typical questions under consideration for dental restoration procedures include: Are esthetics a main concern? Is the patient a bruxer (i.e., heavy grinder)? What is the extension of the patient's smile—give the teeth numbers of the limits of what is visible on their widest smile? Does the patient have a high lip line, i.e., does their lip lie below the incisal edge, midtooth, at the cervical margin, above the cervical margin? Do they show mandibular (lower) teeth when they smile? Is the opposing occlusion natural? If not, is it metal, porcelain, amalgam, composite or denture teeth? By providing the restoration lab with this additional information, all factors can be considered so that a sound, tailored treatment plan can be confirmed or recommended.

The laboratory then would consider the teeth in question: Are they anterior or posterior? Endodontically treated or vital? What shade are they initially? What is the desired shade? What is the prepared tooth shade? What are the dimensions of the tooth—is it a short clinical crown, or average to larger than average in size? Are there any implants involved? The process would operate like an "elimination tree"—if the first question of esthetic concern was a "no", the site would not go on to ask smile dimensions and such. All questions would be answered to a point to compile a profile, and any given patient may require their case to be divided into more than one profile depending on the scope of their needs, say corresponding to sections of their mouth in quadrants Another issue to be addressed is that of materials. This would give the material name, its characteristics and properties, and why it was suggested. Suggested is the operative word here because it should be understood that ultimately it is the dentist's choice of treatment modality that is used and not that of the technician or the site. After the dentist chooses the material, he would need to know where to obtain it, if he didn't already have access to it. This would entail the dentist purchasing a direct material, either through the site to an ordering area, or being referred to a lab in his area that uses such a system.

The issue of preparation design when planning to use that given material is also addressed by the site. Different materials demand different substructures and margins. There are not a tremendous number of different designs needed. Within the site, there is a file of preparation diagrams, which could be printed out by the dentist, if necessary, to provide reduction dimensions, margin design and the burs needed to do this. This would include bur name and number, type and where to obtain them. Once again, the dentist may order this through the site or obtain information on where it could be purchased in his area. The dentist could simply obtain all materials from the site, compile a shopping list for this particular procedure and go out and obtain the materials on his own.

Once the case is underway, and the initial preparations are completed, the dentist could go back to the site and scan the preparations to assure compliance. Alternatively, digital representations of the preparations could be sent back to the site or lab for their further review. A review of the preparations can also be made by accessing a survey area of the site. This would evaluate the preparation for undercuts, under-reduction, margin extension, and highlight areas that needed to be modified for optimum results.

Communication with the site in real time would save a great amount of time and effort. By first confirming that the preparations and recommended dental restoration procedures are correct, the lab would not have to be pouring and working on models of a case that were not useable because the preparations required changing. Also saved would be the time of having the patient return to the office on multiple occasions for refining preparations. This is a significant benefit for dentist, patient and laboratory. By providing the laboratory operator with such information without taking an impression, pouring up models and surveying them with a traditional surveyor, both time, materials and expenses due to re-work are saved.

Another advantage of real time evaluation is reduction. One of the most common errors in preparation is under-reduction (i.e., not removing enough tooth structure to allow room for the materials that will make up the crown or restoration), which causes either too thin of restoration in that area which can lead to future failure, or repreparation (i.e., more wasted chair time) and new impressions or reduction copings. Within the survey site, the dentist would be able to more accurately scan the preparation with the teeth in occlusion so as to measure the amount of reduction to the tenth of a millimeter. Then, the dentist would compare this measurement to the given specifications of the preparation he had retrieved earlier from the preparation design area of the site to confirm compliance.

Another use of the present interactive dental restoration network is the verification of the final dental prosthesis before it is permanently placed in the patient's mouth. For example, when a crown is finally prepared, digital images can be taken and compared to the digital images of the patient's teeth that were previously obtained to assure that the closest color match has been achieved. Any necessary color corrections can be made by the laboratory or the technician before permanent placement of the crown. This again saves time by avoiding rework when the patient returns to the dentist's office for the installation of the crown.

A number of different aspects of determining tooth shade color are disclosed. For clarity of presentation, these aspects are organized and described below in sections which are not intended to be limiting in any way.

The Color Determination Method

Figure 2:
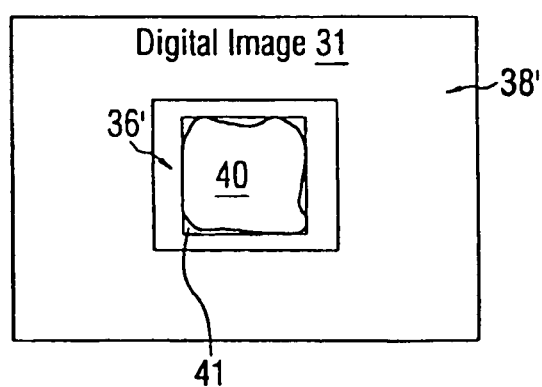
FIG. 2 shows a representative image captured by the system of FIG. 1.

With reference to FIG. 1, a solid state camera 12 (e.g., a CCD camera coupled to a PC board, or an intra-oral camera) is utilized to capture one or more images of each known conventional tooth shade. Tooth shades used to this end may correspond, for example, to the VITA™ Shade guide, or a shade guide corresponding to porcelain by another dental products manufacturer. By way of example, a first series of images taken in accordance with the invention corresponds to sequential images of the A1 shade by Vita, a second series of images corresponds to sequential images of the A2 shade by Vita, and so on. In accordance with the invention, captured image series of the known tooth shade guides are properly labeled and then stored onto the hard disk of the computer, or other suitable storage device for further analysis. FIG. 2 illustrates a representative digital image 30 captured by the camera 12.

As known in the art, each digital image has a plurality of picture elements, i.e., "pixels", corresponding to the elements of the solid state camera and representing the light intensity and color properties of a given spatial location on the tooth. The distance between adjacent pixels in the image is determined by the spatial resolution of the camera. For example, an image of a tooth shade (or a human tooth) can be made up of 300 pixels in width across the tooth and 350 pixels in height. In human teeth, any given tooth is approximately the same size, give or take a couple of millimeters, for all people. For example, most central incisors usually measure between 9-11 mm in width, and somewhat greater in length. It is clear therefore that for a given spatial resolution of the camera, in accordance with this invention an image of a tooth can be taken knowing the approximate number of pixels corresponding to the tooth in the image. Thus, in the example above, 1 mm of the tooth width may be represented by 30 pixels. It will naturally be appreciated that the tooth image is typically not rectangular, and that pixels at the corners 41 of an image may correspond to the background (i.e., the region outside of the tooth) and not of the tooth or tooth shade. See FIG. 2 for further illustration.

As indicated above, a single digital image can be captured for each tooth shade or actual tooth. Those skilled in the art will appreciate, however, that taking a series of images per shade is preferable, since it reduces the risk of image anomalies, as explained in further detail below.

Figure 3:
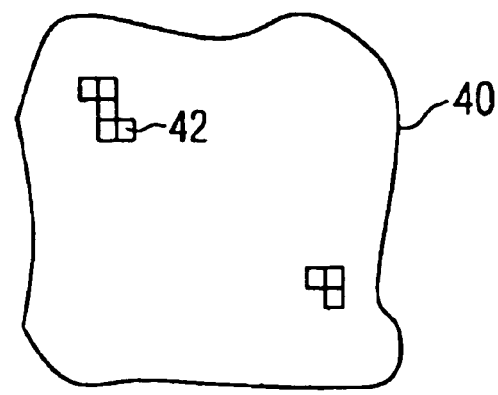
FIG. 3 shows a representative image made up of pixels as captured by detector elements of the system in accord with the invention.
Figure 4:
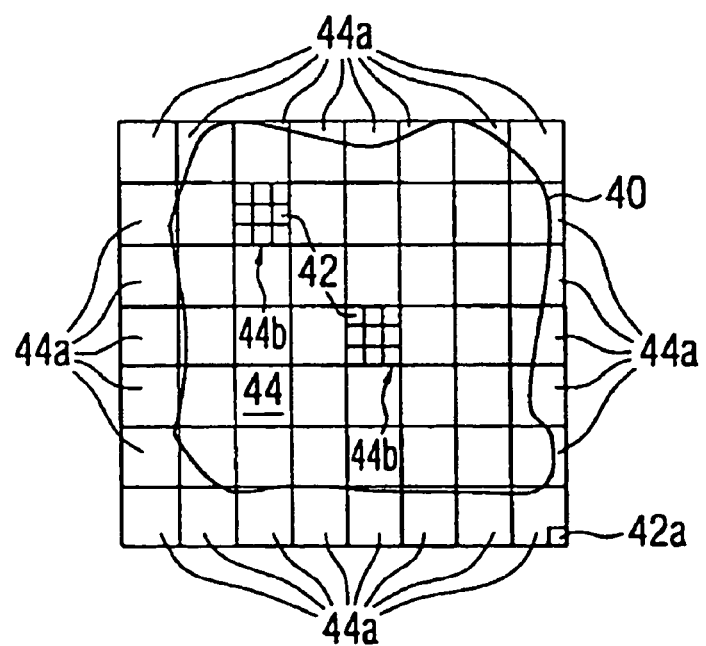
FIG. 4 illustrates processing of the image of FIG. 3 using pseudo-pixels, in accord with one preferred embodiment of the invention.

Next, each image or each image in a series is processed into a "pseudo" reference image (hereinafter PSEUDO IMAGE) made up of pseudo-pixels. As used in this disclosure, pseudo-pixels correspond to groups of pixels covering specific areas (e.g., rectangular or square) of the image plane. FIG. 3 shows a blow up image of the pixels 42 (only representative pixels 42 are shown) which make up the tooth image 40 of FIG. 2. In accord with the invention, these pixels are transformed into pseudo-pixels 44, as shown in FIG. 4. In the embodiment illustrated in FIG. 4 each pseudo-pixel 44 is made up of all or some of the real pixels within the area of the associated pseudo-pixel. Pseudo-pixels 44b shown in the figure illustrate, for example, how a pseudo-pixel can be generated from nine real pixels 42. FIG. 4 also illustrates that an image can be made from either a real tooth 40 (resulting in a REAL IMAGE) or a reference shade 40 (resulting in a REFERENCE IMAGE).

Figure 9:
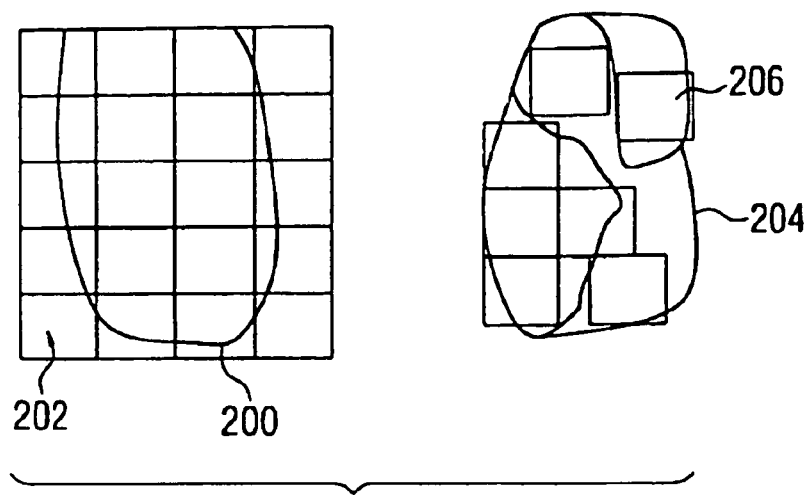
FIG. 9 illustrates different pseudo-pixel imaging mechanisms, optionally dependent upon tooth shape characteristics, used in accord with the invention.

FIG. 9 shows how pseudo-pixels can be arranged in a preferred embodiment in different patterns, automatically, depending upon which tooth is imaged. For example, an incisor 200 can have an arrangement of pseudo-pixels 202, as shown in the left-hand example, while a molar 204 can have an arrangement of pseudo-pixels 206, as shown in the right-hand example. With further reference to FIG. 1, such arrangements can be made automatically in the system of this invention by informing the computer 14, and hence the software 50, to apply pseudo-pixels in the appropriate pattern. Such arrangements assist in overall processing by ensuring appropriate pseudo-pixel placement. As illustrated in FIG. 9, pseudo-pixels need not be contiguous, or aligned, such as shown by the arrangement of pseudo-pixels 206.

In a preferred embodiment, the intensity and color associated with a pseudo-pixel are computed or otherwise formed as an average (or other statistical measure) of the actual pixels forming the pseudo-pixel. By way of example, if an actual image taken in the first step of the method corresponds to a rectangular tooth that is digitized at 300 W by 350 H resolution, i.e., having a total of 300×350 elements, in accordance with this embodiment one can create pseudo-pixels such as 6 W by 7 H, with each pseudo-pixel being formed as a statistical measure of the 50×50 pixels within the pseudo-pixel (resulting in 42 pseudo-pixels representing the entire tooth).

As noted above, in accordance with a preferred embodiment, pseudo-pixels are generated by data derived from all or some of the actual pixels located within the pseudo-pixel. For example, in a specific embodiment one can average the red, green and blue (RGB) components for each of the 2500 pixels within each pseudo-pixel to determine a reference RGB for that pseudo-pixel. Those skilled in the art will appreciate that other statistical measures or characteristics can be used, such as the mean "hue" measure of the pixels within a pseudo-pixel, or others. For example, the RGB pixel values may be converted into the Hue, Saturation and Intensity ("HSI") color space by using known algorithms, such as the Gonzalez and Woods method, as follows:

R=Red value for pixel
G=Green value for pixel
B=Blue value for pixel
Intensity=⅓ (R+G+B)
Saturation=1−(3/R+G+B))*Min(R, G, B)
Hue=$Cos^{-1}((0.5*((R-G)+(R-B)))/((R-B)*(G-B))^{0.5})$
If S=0, Hue is meaningless
If (B/Intensity)>(G/Intensity) then Hue=360−Hue
RGB corresponds generally to three different pixels
Since Hue is an angle in degrees values were normalized to 0.1 with Hue=Hue/360

As known in the art, the RGB color space can be represented as a simple cube, with R, G and B emanating from one corner along three perpendicular edges. The origin corner (0,0,0) is black, and the opposite corner (1,1,1) is white. All points along this line from corner to corner are shades of grey. The HSI color space is this same cube stood on the origin corner, with the Black White line being vertical. The black-white line is the intensity axis, the hue is given by an angle from the intensity axis and the saturation is the distance from the intensity axis to the color point (i.e., the radius). The new VITAPAN 3D-Master Shade system uses an L*a*b* Color Sphere to determine tooth shades based on Value, Chroma and Hue. It is possible to convert the RGB values to this color system, if necessary or desired.

In accordance with a preferred embodiment, PSEUDO IMAGES are processed then into a "REFERENCE IMAGE". By way of example, the REFERENCE IMAGE is generated as an average (or other statistical measure) of the PSEUDO IMAGE series of images of the VITA™ A2 shade guide. The measure in this example is obtained by averaging the R, G, B components for each pseudo-pixel of the A2 PSEUDO IMAGE series to determine an average RGB value for a pseudo-pixel of the REFERENCE IMAGE. In alternative embodiments operating in the HSI color space, the corresponding average values can also be determined for each pseudo-pixel of the PSEUDO IMAGE series; and, for example, an average hue (or other statistical measure of hue) can also be associated with each pseudo-pixel in the REFERENCE IMAGE. Those skilled in the art will appreciate that other color characteristics can be used alternatively or in conjunction with the measure of RGB and/or hue. It will be appreciated that if only one PSEUDO IMAGE is made per shade, then that PSEUDO IMAGE defaults as the REFERENCE IMAGE since no other statistical combination is available.

It should be noted that forming of pseudo-pixels is not a requirement for practicing this invention. However, pseudo-pixels are used in a preferred embodiment because they may reduce the processing load of the system, minimize storage requirements and also because they can simplify the task of aligning corresponding pixels from different images. Proper pixel alignment is important in order to ensure the integrity and accuracy of the statistical averages used in the formation of REFERENCE IMAGES. In this regard it will be appreciated that it is generally difficult to precisely align all pixels in several images taken from the shades of the same shade guide, unless there is extremely good control utilized in the image capture sequence. Using pseudo-pixels in accordance with the preferred embodiment reduces the total number of pixels per image and thus simplifies the task of aligning different images accurately.

Pseudo-pixels are even more important in later steps of the processing method of this invention. That is, although one has complete freedom to set up the optics and the camera, which together determine the magnification of a captured tooth shade (or tooth) image, when trying to "match" a REFERENCE IMAGE to an actual digital image of a patient's tooth, the actual image (hereinafter referred to as a SNAPSHOT) may be quite different in shape and size (either real size or apparent size due to magnification differences in the optics or camera CCD element size). As such, a "one-to-one" comparison between the SNAPSHOT and the REFERENCE IMAGE is difficult. Pseudo-pixels help in this respect because the SNAPSHOT can be scaled to approximate the REFERENCE IMAGE size, or vice versa; and the SNAPSHOT can also be processed into pseudo-pixels. The scaled and pseudo-pixel version of the SNAPSHOT image is denoted as the "REAL IMAGE" hereinafter. Pseudo-pixels used in a preferred embodiment thus permit a convenient mechanism for comparing a REFERENCE IMAGE to a REAL IMAGE.

In accordance with a preferred embodiment, the generation of each REFERENCE IMAGE preferably includes a "bad pixel" routine where each pseudo-pixel in the PSEUDO IMAGE series is analyzed for bad pixels. A "bad pixel" means any real pixel corresponding to a defective CCD element or corresponding to an area with an unwanted artifact, e.g., reflection, in the digital image, or an area that contains "background" imagery (e.g., any pixel image not corresponding to the tooth or tooth shade). Any pseudo-pixel in the PSEUDO IMAGE which contains a bad pixel is preferably not utilized in the generation of the REFERENCE IMAGE. That is, if for example a REFERENCE IMAGE is made up as an average of three PSEUDO IMAGES, and yet one pseudo-pixel in one of the PSEUDO IMAGES contains a bad pixel, then in a specific embodiment the resulting pseudo-pixel of the REFERENCE IMAGE is either discarded, or computed only as an average of the other two associated pseudo-pixels of the PSEUDO IMAGES.

Note that the bad pixel routines are particularly important at the edges of the image of the tooth or tooth shade. Consider, for example, the shape of the tooth 40 in FIG. 3 or the irregular shapes illustrated in FIG. 14. Clearly, such shapes are not rectangular, and thus creating pseudo-pixels in accordance with the preferred embodiment will result in certain pseudo-pixels having bad pixels at the image edge. FIG. 4 illustrates bad pseudo-pixels 44a that contain pixels 42a, which are not part of the tooth image 40. Bad pixel routines used in accordance with a preferred embodiment to detect such pixels and disqualify them from further processing. For example, if 5% or more of the pixels within a pseudo-pixel are "bad" (e.g., containing reflections or other unwanted data), then such pseudo-pixels are disqualified. Though not shown, other pseudo-pixels might be disqualified if for example reflections from the light ports cause unwanted reflections in the other pseudo-pixels image 40. In a preferred embodiment, such pseudo-pixels are deleted from inclusion in the REFERENCE IMAGE.

In a specific embodiment, the bad pixel routine need only be implemented when capturing and generating REAL IMAGES. In that process, conditions such as lighting and other variables can create unwanted artifacts that should be eliminated from processing. In addition, when cameras are used in the field, one pixel might become defective over time; and REAL IMAGES later generated from the defective camera should be adjusted so that the pseudo-pixel which contains the bad pixel is not counted or utilized.

In another aspect, areas of the tooth for which the color is to be evaluated are predefined, allowing the analyzer program operating in accordance with this invention to batch-process the images. For example, a sample image can be loaded into an Area Selection Editor program module, where adjustments can be made to user-selected (or predefined) areas of the tooth image. These defined areas are then applied to each image in turn, and the pixel colors within each area are analyzed. In operation, following the image capture in one embodiment the method of this invention proceeds to automatically select the area(s) of the sample for analysis, for example, by applying a general rule to locate the edges of the tooth in the image, and applying a predefined segmentation of the remaining area for analysis. Preferably, the user is allowed to manually select an area of interest in the image, for example, using a computer mouse, as known in the art.

In accordance with one embodiment, following the detection of the correct areas for analysis (i.e., excluding edges, light reflections and other unwanted artifacts), the selected area is divided by using, for example, a grid overlay, as shown in FIG. 9. As known, each shade has varying color content from top to bottom. Therefore, in accordance with this embodiment a more accurate analysis of the entire surface of interest can be made if color determination and matching is applied to the individual cells of the grid, as compared with corresponding area cells of the stored color reference model for each shade guide.

Following this stage, in a preferred embodiment before analyzing the area, various filtering operations can be applied to the image, as known in the art. For example, filtering is applied to eliminate abnormalities such as lamp reflections or dark spots. In addition, maximum, minimum and average values for the R, G and B components can be determined over the area of interest and used to, for example, limit the variation from the average value to half way to the maximum and minimum values. This simple filtering operation has shown satisfactory results in actual testing, although alternative or additional filtering operations can be applied, as known in the art in order to obtain a standard image.

In the next step of the method, a SNAPSHOT of a patient's tooth is taken by the camera. Next, the digital image of the SNAPSHOT is scaled, if necessary, to approximate the size of the corresponding REFERENCE IMAGE. In the preferred embodiment SNAPSHOT pixels are next processed into pseudo-pixels resulting in a REAL IMAGE containing pseudo-pixels, which substantially correspond to REFERENCE IMAGE pseudo-pixels. A bad pixel routine preferably processes the REAL IMAGE to delete REAL IMAGE pseudo-pixels containing a bad pixel. As above, the bad pixel routine is particularly important at the edges of the tooth image within the SNAPSHOT, where some pixels will certainly contain background (unless the camera and optics are arranged to capture only the tooth; however this is not efficient since effective matching between the REAL IMAGE and the REFERENCE IMAGE occurs when a larger area of the tooth is used in the comparison algorithms, which are defined in further detail below).

In a subsequent step, the REAL IMAGE is compared (i.e., correlated) to each REFERENCE IMAGE in the database (e.g., there could be sixteen REFERENCE IMAGES corresponding to the A1-A4, B1-B4, C1-C4 and D2-D4 Vita Shades) via the correlation algorithm (hereinafter "Correlation Algorithm") described below. In this step, each pseudo-pixel of the REAL IMAGE is compared to each pseudo-pixel of the REFERENCE IMAGE; and a composite match number ("CMN") is created indicating how well the REAL IMAGE matches to that REFERENCE IMAGE. The composite match numbers are compared to one another and one of the REFERENCE IMAGES is selected as the "best fit" match to the REAL IMAGE.

There is potentially a problem associated with the bad pixel routine and subsequent correlation between REAL IMAGES and the series of REFERENCE IMAGES. As described above, in a specific embodiment, when there is a bad pixel in any pseudo-pixel, all other pseudo-pixels of the same spatial location are discarded. This can become a problem in a case when every (or even most) pseudo-pixel is disqualified, resulting in a situation where no meaningful comparison can be made. Accordingly, in a preferred embodiment, images are correlated on the basis of mathematical measure, i.e., an average, that is functionally dependent upon how many pseudo-pixels remain in an image (REAL or REFERENCE). That is, for any given correlation between a REAL IMAGE and a REFERENCE IMAGE, the number of pseudo-pixels for that comparison is used as a ratio for comparison to other correlation. This aspect of the invention is described in more detail below.

In an alternative embodiment, the averaging technique discussed above is used only when, for example, more than 20-25% of the pseudo-pixels are disqualified for all comparisons. Accordingly, so long as there is a sufficient number of remaining pseudo-pixels for comparison, a direct comparison of these pixels can be made without resorting to averages. In a specific embodiment, a sufficient number is deemed to be about 75-80% of the total number of pseudo-pixels available for comparison. Other ratios can be used in alternate embodiments.

Bad pixel routines are generally known in the art and thus need not be described in much detail. It is sufficient to note that in accordance with this invention a pixel is determined to be "bad" if its light intensity or color values deviate by more than a certain predefined percentage from adjacent pixels known to be "good". For example, if a pixel deviates by more than 30% from the light intensity of the neighboring 8 pixels, there is a good likelihood that this deviation is anomalous, i.e., due to a bad camera element or corresponding to an image border, and has to be discarded.

In a preferred embodiment, a pseudo-pixel is validated only when it contains less than a certain percentage, i.e., about 5%, bad pixels of the total pixels making up the pseudo-pixel. Preferably, bad pixels are also not used in the statistical characterization (e.g., RGB) of the pseudo-pixel. Accordingly, in this embodiment if more than about 5% bad pixels exist for a pseudo-pixel, the pseudo-pixel is not used in further processing.

Correlation Algorithms

In a preferred embodiment, the Correlation Algorithm of the present invention operates as follows. Each REFERENCE IMAGE is actually a matrix of vectors, each vector corresponding to a pseudo-pixel. By way of example, the REFERENCE IMAGE corresponding to the A1 Vita Shade can be assigned as vector $Z_{A1}$. For the sixteen Vita Shade guide, the remaining fifteen shades for example each have a REFERENCE IMAGE too, e.g., $Z_{A2}$, $Z_{A3}$, etc.

Each REFERENCE IMAGE vector "Z"—corresponding to shade guide or porcelain "X"—thus has data similar to the following matrix:

$$Z_x = \begin{vmatrix} PP_{x,1} \\ PP_{x,2} \\ PP_{x,3} \\ \ldots \\ PP_{x,n} \end{vmatrix} = \begin{vmatrix} R_{x,1} & G_{x,1} & B_{x,1} \\ R_{x,2} & G_{x,2} & B_{x,2} \\ R_{x,3} & G_{x,3} & B_{x,3} \\ \ldots & \ldots & \ldots \\ R_{x,n} & F_{x,n} & B_{x,n} \end{vmatrix}$$

where each of the pseudo-pixels "PP" has three values for each of R, G and B values of the pseudo-pixel (actually, the RGB values are the statistically computed (e.g., averaged) composition of the images in the series for that REFERENCE IMAGE, if available). The subscript "x" refers to the appropriate shade, e.g., "A1". Subscripts 1-n define separate pseudo-pixels in the REFERENCE IMAGE. Those skilled in the art will appreciate that additional, other or different data can make up each vector, including hue data for each pseudo-pixel. Additionally, other vectors can be considered and processed in the correlation, such as hue and RGB values.

In a typical example, each REFERENCE IMAGE might have 20×20 pseudo-pixels which define the REFERENCE IMAGE. Therefore, "n" in the above matrix is 400.

When a REAL IMAGE "I" is generated, in accordance with this invention it too is arranged as a matrix of similar form, with each pseudo-pixel "PI" of the REAL IMAGE being a vector of RGB form (or, like above, containing other or additional factors such as hue):

$$I = \begin{vmatrix} P_{x,1} \\ PI_{x,2} \\ PI_{x,3} \\ \ldots \\ PI_{x,n} \end{vmatrix} = \begin{vmatrix} R_{i,1} & G_{i,1} & B_{i,1} \\ R_{i,2} & G_{i,2} & B_{i,2} \\ R_{i,3} & G_{i,3} & B_{i,3} \\ \ldots & \ldots & \ldots \\ R_{i,n} & F_{i,n} & B_{i,n} \end{vmatrix}$$

In a specific embodiment, the Correlation Algorithm used in accordance with the present invention computes a measure of closeness, i.e., a composite match number ("CMN") through the following relationship:

$$CMN_x = \sum_{q=1}^{n} \sqrt{(Z_{x,q} - I)^2} = \sum_{q=1}^{n} \sqrt{(PP_{x,q} - PI_q)^2}$$

or $$CMN_x = \sum_{q=1}^{n} \sqrt{(R_{x,q} - R_{i,q})^2 + (G_{x,q} - G_{i,q})^2 + (B_{x,q} - B_{i,q})^2}$$

Once the CMN number is computed for each tooth shade, as shown in the example above, a search is then conducted for the lowest CMNX to find the best fit REFERENCE IMAGE for the REAL IMAGE. That is, the tooth shade or porcelain "X" is identified for the lowest associated value of CMN. As noted above, if there are more than a certain percentage of bad pixels in any pseudo-pixel q for either the REFERENCE IMAGE or the REAL IMAGE, in a preferred embodiment that pseudo-pixel is not used in the valuation of CMN. For example, in accordance with the present invention it is acceptable to determine CMN without the q-th pseudo-pixel; however, every other concurrent q-th pseudo-pixel valuation of CMNX in identifying the composite match number is also discarded, so that CMNs for all tooth shades can be compared correctly.

As noted, the Correlation Algorithm of the embodiment illustrated above preferably uses a bad pixel routine to disqualify bad pseudo-pixels. It was noted already that this can create problems in certain situations. Accordingly, in a preferred embodiment, the following alternative algorithm can instead be used:

$$CMN_x = \sum_{q=1}^{n} \sqrt{\left(\frac{R_{x,q} - R_{i,q}}{Pcount_x}\right)^2 + \left(\frac{G_{x,q} - G_{i,q}}{Pcount_x}\right)^2 + \left(\frac{B_{x,q} - B_{i,q}}{Pcount_x}\right)^2}$$

In this embodiment for the computation of CMN $Pcount_x$ corresponds to the number of common pseudo-pixels found between the REAL IMAGE and the vector $Z_X$. Note that $Pcount_x$ can be different for each CMN correlation. For example, if the REAL IMAGE has 400 pseudo-pixels, all good, and REFERENCE IMAGE for A1 has 399 pseudo-pixels (e.g., one bad pseudo-pixel identified in the bad pixel routine), then $Pcount_{A1}$ is 399. If however the REFERENCE IMAGE for B4 has 256 pseudo-pixels, then $Pcount_{B4}$ is 256. If in the same example the REAL IMAGE has 256 valid pseudo-pixels—and in the unlikely event that the disqualified REAL IMAGE pseudo-pixels overlap with the coordinates of disqualified pseudo-pixels in the REFERENCE IMAGE—then $Pcount_{B4}$ is still 256; however $Pcount_{A1}$ is also 256 (assuming that the one bad pixel of REFERENCE IMAGE A1 corresponds to one of the disqualified pseudo-pixels in the REAL IMAGE). If the one bad pseudo-pixel in REFERENCE IMAGE A1 does not correspond to coordinates of one of the disqualified pseudo-pixels of the REAL IMAGE, a more likely event, then $Pcount_{A1}$ is also 255.

Those skilled in the art will appreciate that isolating the measure of closeness CMN in one of the above equations can also be determined without the square root operation—as a minimum composite match number will still be identified for the same functional conditions and/or data.

In accordance with the specific embodiment described above, the process of determining $Pcount_x$ can be made at any point. In a preferred embodiment, this process is initiated only after a certain percentage of pseudo-pixels are disqualified. For example, if after the completion of the bad pixel routine there remain 300 pseudo-pixels for comparison (in the example that 400 pseudo-pixels exist in each of the REFERENCE and REAL IMAGES), then a straight comparison can be made without the use of the $Pcount_x$ adjustment, because a significant percentage of the images can be compared (defining 75% as "significant"; other percentages can be used). Note that it is likely that many of the bad pixel areas in images will overlap, such as at the edge of the image, where tooth shape variations occur often, and at locations such as reflection areas (e.g., areas which specularly reflect light energy to the camera), which are likely to be similar given that the illumination source is generally fixed for each image acquisition.

Those skilled in the art will appreciate that variations to the above-described methodology may occur without departing from the scope of the invention. For example, other color detection techniques can be used to characterize tooth color within a pseudo-pixel. In one example, calorimetric "laser-diode" measurements can be used to generate a reflection trace for each pseudo-pixel. In such measurements, a laser diode is "scanned" in wavelength so that a laser beam, scanned through a range of wavelengths, reflects off of each pseudo-pixel. This spectrophotometric-like trace information (for example containing reflectance per wavelength) can be collated with other such traces for other pseudo-pixels to generate a vector of such information. As above, correlation between real and reference vectors is used to determine a best-fit color match.

In accordance with another embodiment of the present invention, the camera used for capturing images has a focal plane array with fewer detector elements as compared to typical high resolution arrays (for example those arrays with 640×480 elements, or megapixel digital cameras). For example, in one embodiment of the invention an array has a relatively small number of detectors, i.e., 20×20, 60×40 or others. Such a camera can alleviate the need for pseudo-pixels, as defined above, since each real pixel generated from each detector covers a relatively large area of the tooth image. In effect, such a camera generates "pseudo-pixels" in each digital frame image. Since fewer detector elements are used in this embodiment, it will be appreciated that the camera's overall cost can be reduced. Those skilled in the art will appreciate that a similar effect may be obtained in an alternative embodiment by using magnification optics that only utilizes a small portion of the camera's array in obtaining the image; however such an approach wastes pixel information which has already been collected.

Those skilled in the art will appreciate that other closeness measures can be used instead of the algorithms described above to achieve a similar result. By way of example, other techniques of measuring similarity between two data sets can be used in determining a measure of how similar or close two data sets are. For example, one can arrange a data set as a vector so that the correlation coefficient is determined as the cosine of the angle between data vectors. Cross-correlation functions or matched filtering can also be used beneficially. The interested reader is directed to any number of books on digital image and signal processing, such as, for example, Netravali and Haskell, "Digital Pictures, Representation and Compression," Plenum Press, 1988. Sections 1.1; 1.2; 1.3; 1.8; 1.9; 2.2; 3.2; and 3.3 of this book are incorporated herewith by reference for background purposes.

In still another embodiment, the shape of the grid of pseudo-pixels defining each tooth is selected in a manner dependent upon how the tooth is positioned in the mouth. For example, an incisor tooth very nearly maps to a shade guide; however, with reference to FIG. 14, a posterior tooth does not, particularly relative to the image capture position of the camera. Further, it will be appreciated that for purposes of improving the appearance of a smile, anterior teeth are considerably more important than those in the posterior of the mouth. Thus, in a preferred embodiment it is desirable to provide more close matches, and correspondingly more dense and accurate grid patterns for the anterior teeth. Accordingly, in a specific embodiment, grid shapes and correlation algorithms can depend upon tooth orientation within the mouth and/or upon generalized tooth shape. In particular, anterior teeth will have a (proportionately) larger number of pseudo-pixels than teeth in the back of the mouth for the same surface area.

An image of a tooth or tooth shade may be analyzed by a flood fill algorithm to find the edges of the target tooth or tooth shade. Using this algorithm, from a point in the image (e.g., in the SNAPSHOT) known to be in the tooth or tooth shade, adjacent pixels are considered only if that pixel is in a valid color range. The maximum extent is then recorded for the search in the X and Y directions, forming the outer limits of the grid. In addition, contrast changes in groups of pixels can be considered and used to determine the extent; but a black border is easy to find.

In accordance with another important embodiment, "tooth shades", as used above, are not used per se in defining a patient's tooth color. Rather, in a specific embodiment, a grid of pseudo-pixels is generated for the patient's tooth; and these (pseudo-) pixels define the porcelain for respective regions of the tooth. Pseudo-pixels are not actually required; and actual pixels can also be used in this manner to define porcelain characteristics for each spatial location in the mouth. Reconstructive tooth material is then specified per pixel or pseudo-pixel. A data file generated from the SNAPSHOT or REAL IMAGE is then processed to specify reconstructive materials with spatial precision, as defined by pixels or pseudo-pixels. An acceptable quantification of RGB values, for example, can be used to tolerance both the measurement and materials specification. For example, by associating error bars with each measure—e.g., R+/−$\Delta$R, G+/−$\Delta$G, B+/−$\Delta$B, where the $\Delta$ quantities are defined within certain practical tolerance limits—reasonable tolerances can be achieved. Tooth shades operate similarly in that each shade results in a quantized color difference from every other shade; and thus the aforementioned tolerancing technique provides similar accuracy to the above-described correlation algorithm. Unlike the tooth shade approach, however, spatial accuracy for any given reconstructive tooth is generally determined only by the number of pixels or pseudo-pixels used in the reconstructive tooth manufacture; whereas a tooth shade has predefined color gradients defining the tooth shade regardless of the numbers of pixels or pseudo-pixels used. It will be appreciated that this approach avoids the use of tooth shades at all, along with the possible confusion created by the existence of alternate tooth shade guides.

The Color Measuring System and Its Components

Cameras of the type required for use with this invention are generally known in the art and include, for example: INSIGHT™, manufactured in San Carlos, Calif.; CYGNASCOPE™ offered by Cygnus Instruments, Inc., Goleta, Calif.; VISTACAM™ and others. In a preferred embodiment, the system of this invention uses a Welch-Allyn brand camera. Generally, it is desired to use camera systems offering full-color imagery, which are capable of capturing a range of sizes, i.e., from the size of a typical patient's tooth preferably to images of the patient's whole smile.

In the preferred embodiment, it is advantageous for the camera to supply a minimum 640×480 pixel image to the PC software at 24 bits per pixel (i.e., 8 bits for each of the red, green and blue (RGB) components), or preferably 30 bits per pixel. In a specific example, the system of this invention uses ALARIS QUICK VIDEO TRANSPORT frame grabber, providing digitized images with at least 24 bits resolution. More specifically, the software can use a Twain protocol interface, as known in the art, which allows other cameras and frame grabbers to be tested without the need for a change of software. Preferably, images captured by the camera are displayed on a monitor screen to provide instantaneous feedback to the system operator.

In another preferred embodiment, the resolution of the camera is specified in terms of the Minimum Resolvable Color Difference that the complete system is able to achieve. This can be specified, for example, as the two RGB values of the two closest shades the system is required to differentiate. For example, the Chromoscop Shades 430 and 440 can be used to this end. In general, it is envisioned that the system should be able to differentiate between about 80 or more different shades. Another requirement is that the system should be able to produce repeatable images. That is to say that images of the same tooth taken at the same session should not have a $\Delta i$ of not more than 0.1, which is the amount needed for the eye to perceive a difference. In a specific embodiment, the camera used in the system of this invention is a CMOS imager.

In terms of its physical setup, a stand-alone camera containing its own light source can be used, as explained below. A number of alternate embodiments are available in this regard. For example, in one embodiment the camera can be battery powered. In this embodiment, the camera sits on a holder containing an inductive battery charger when it is not in use. In another embodiment, when mounted on the charger the camera can be coupled via an isolation sleeve (to be explained below) to a calibration target, for example, made of porcelain.

In a specific embodiment the output of the camera is supplied to a digitizer (such as a Sony digitizer) enabling convenient digital storage of the image. As noted above, the output of the camera can also be supplied to a frame grabber in a PC. Both options can be used in a specific embodiment. In another embodiment, the output of the camera can be supplied directly to a monitor (preferably positioned close to a surgery chair) and provide a digital output to a PC, which then need not be close to the patient. As known in the art, the output could be USB-type, or IEEE 1394.

In accordance with a preferred embodiment the digital output of the camera also provides the opportunity to control the camera from a PC. Finally, in a preferred embodiment it is desirable to control the camera so as to use it in two modes, i.e., normal image—for the mouth and full face shots; and analysis image—in which color balance and automatic functions are disabled for tooth and calibration image, as described below.

Turning now to the drawings, FIG. 1 shows a system 10 constructed according to a preferred embodiment of the invention. A solid state (or intra-oral) camera 12 connects to a computer 14 via a PC card 16 to capture images through a wand 18. The solid state camera 12 includes a detector array 12a including an array of detector elements 12b, which generate pixels in the digital images (e.g., SNAPSHOTS) captured by the camera 12.

Through one of several known mechanisms, internal optics within the wand 18 and/or camera 12 permit the capture of an image of a target object 20 (for purposes of illustration, target object 20 is shown grossly over-sized as compared to other elements in FIG. 1) by the array 12a. By way of example, relay optics 18a within the wand relays an image to the array 12a. A protection sleeve 22, discussed in further detail below (also grossly oversized for purposes of illustration), preferably extends from the wand 18. As shown, the optics provide an optical conjugate between the array 12a and the target object 20 through well-known imaging techniques. Light captured from the target object 20 enters the wand 18 for transfer to the camera 12 through an entrance aperture window 26.

The wand 18 generates light 19 to illuminate the target object 20 through light ports 28. Preferably, light from the outside 30 of a sleeve 22 is not permitted to illuminate the object 20 so that control is maintained; and thus the sleeve 22 shields the target area 20 from illumination by outside sources 30 (e.g., ambient room lighting).

An aperture 32 within the center of the end piece 34 of the sleeve 22 is where the tooth or tooth shade are placed so that a SNAPSHOT (i.e., a digital image of the tooth or tooth shade) can be made. As discussed above, these SNAPSHOTS are processed to form REAL IMAGES (from real teeth) or REFERENCE IMAGES (from tooth shades or porcelains, etc.).

A black border 36 around the aperture 23 provides a good reference around which the tooth or tooth shade are discernible within the digital image of the target area 20. The remaining area 38 about the border 36 and within the end piece 34 is preferably a white reference sample, equally reflecting all light 19 from the light ports 28.

Finally, again with reference to FIG. 1, digital images from the camera 12 are sent to the computer 14; and processing software 50 within the computer 14 processes these images to generate a CMN for each REAL IMAGE relative to the REFERENCE IMAGES. As discussed above, the software 50 processes the CMNs to locate the lowest value CMN, indicating a match; and communicates the associated shade of that lowest CMN to the user via signal line 52. As mentioned, other processing algorithms can be developed to determine a best-fit match without departing from the scope of the invention.

A representative digital image 31 captured by the camera 12 is illustrated in FIG. 2, showing an image 36' of the border 36, an image 38' of the reference sample 38, and a tooth image 40. The entire image 31 covers the target area 20 of FIG. 1. FIG. 2 also illustrates obvious regions 41 of the image 31 that would generate bad pixels since such regions do not contain tooth imagery but rather other background imagery (e.g., the patient's gum).

FIG. 3 shows a blow up image of the pixels 42 (only representative pixels 42 are shown), which make up the tooth image 40 of FIG. 2. In accord with the invention, these pixels are transformed into pseudo-pixels 44 of FIG. 4. Each pseudo-pixel 44 is made up of all or some of the real pixels within the area of the associated pseudo-pixel 44. Two pseudo-pixels 44b illustrate, for example, how a pseudo-pixel can be generated from nine real pixels 42. FIG. 4 also illustrates that an image can be made from either a real tooth 40 (resulting in a REAL IMAGE) or a reference shade 40 (resulting in a REFERENCE IMAGE). REAL IMAGES and REFERENCE IMAGES are correlated to find the composite match number (CMN) as described above.

Figure 5:
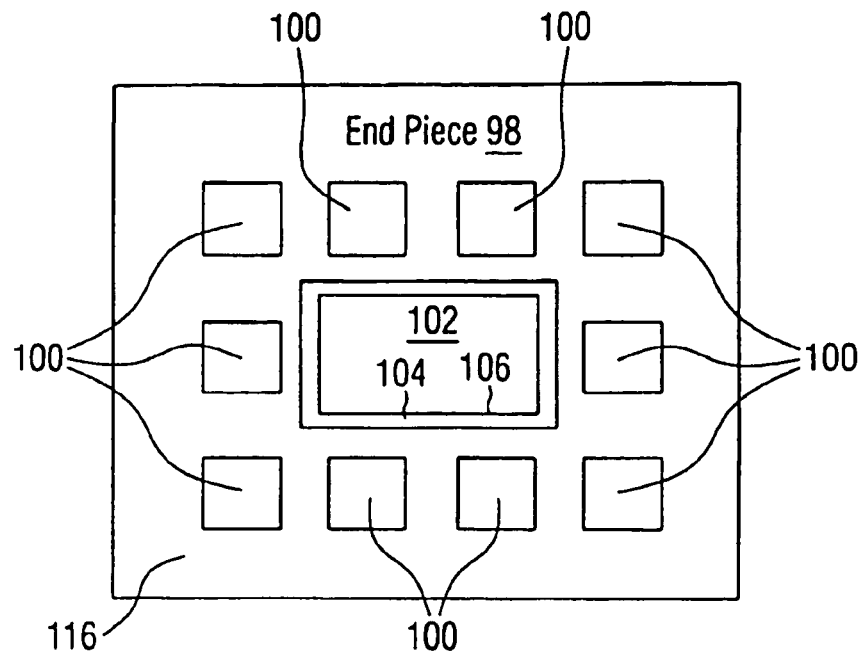
FIG. 5 shows an end piece constructed for use with the system in FIG. 1, for simultaneous processing of an actual tooth image and various reference tooth shades.

FIG. 5 shows another embodiment of an end piece 98 used in accordance with a specific embodiment, that mounts to, or is made integrally with, the end of the sleeve (e.g., the sleeve 22, FIG. 1) and which has a series of tooth shades 100 disposed in the end piece 98, so that for each target 102 (e.g., the tooth or tooth shade), all relevant manufacturing shades are provided in the same digital image, thereby preventing color contamination or other anomalies caused by time delay. As discussed above, when using the end piece 98 of this embodiment each shade 100 is processed as a REFERENCE IMAGE and the tooth 102 is processed as a REAL IMAGE relative to those REFERENCE IMAGES to find a CMN. Preferably, a black border 104 surrounds the tooth aperture 106 and tooth 102. Also preferably, the remaining area 116 about the border 104 and in the end piece 98 is a reference area. By way of example, the reference area 116 is a white reflecting region which can be sampled by detectors that image that region 116. Further examples of the use of reference area are discussed below.

Isolation Sleeve

In a preferred embodiment, an isolation sleeve is used to reduce variations in the images captured and processed by the system, and in particular to eliminate light contamination from external sources. In addition, the isolation sleeve preferably keeps the reference shade and the actual tooth at a set distance from the illumination source and the camera optics. The sleeve also preferably sets the angle of illumination between the source and the tooth so as to reduce reflections. More particularly, the REFERENCE IMAGES and the REAL IMAGE are preferably taken at the same illumination intensities, at approximately the same distance, and without substantial specular reflections from the source. To this end, in a preferred embodiment the sleeve shields the camera detector from imaging outside light and instead utilizes internally generated light (i.e., internal to the camera, for example, or associated with an intra-oral wand attached to the camera) that can be controlled. The sides (or side) of the sleeve are coated in a specific embodiment with a black material (e.g., a paint or a black mat paper, or black felt), which reduces reflections along the sleeve to the tooth or reference shade. As used herein, "target area" refers to the image gathering location that the system of the invention (i.e., that region captured by the camera's detectors), including the REAL or REFERENCE IMAGE, as defined above.

Figure 6:
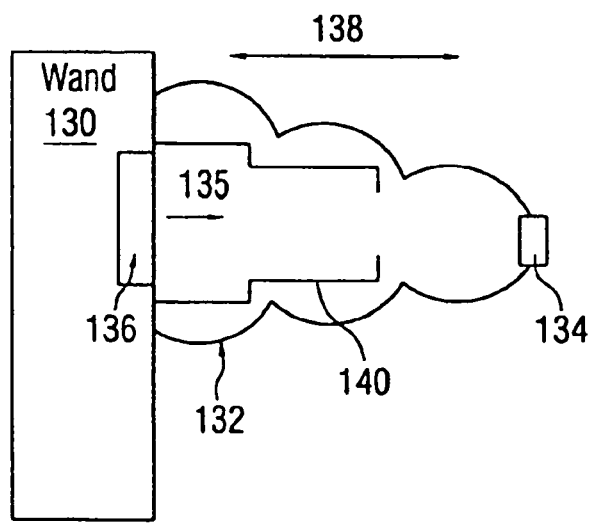
FIG. 6 illustrates a compression sleeve constructed according with a specific embodiment of the invention for capturing high-quality tooth images.

FIG. 6 shows one end of wand 130 and a sleeve 132 constructed according to a specific embodiment of the invention. As in the example shown in FIG. 1 above, the wand 103 connects to a solid state camera (not shown, for purposes of illustration) to collect digital images of the target region 134 at the end of the sleeve 132. By way of example, the target region 134 includes an aperture (not shown) for imaging a tooth therein. Light 135 from the camera or wand 130 exits the wand 130 at optical aperture 136 to illuminate the target region 134.

In a specific embodiment illustrated in FIG. 6, the sleeve 132 used in the camera system of the present invention includes an accordion-like exterior, which permits soft placement of the end of the sleeve onto the patient's tooth. Preferably, such a sleeve is not entirely rigid so that the sleeve 132 can make contact without concerns about damaging the tooth. The outer portion of the sleeve 132 in this embodiment thus acts similar to a spring, and an inner structural member within the sleeve sets the final source-to-tooth distance once the outer sleeve/spring compresses to the desired location.

As shown in FIG. 6, the accordion-like sleeve 132 compresses between the target region 134 and the wand 130, as shown by compression arrow 138. In operation, a user of the wand/sleeve 130/132 pushes the sleeve 132 to the patient's tooth, and the sleeve 132 compresses to provide comfortable (i.e., non-rigid) contact with the tooth. In a preferred embodiment, the sleeve 132 is spring-like to provide some force opposing compression. This force increases until there is an interaction between the sleeve 132, and/or the end piece of the sleeve 132 (i.e., the part of the sleeve at the target region 134), and the rigid structural member 140 within the sleeve 132. The member 140 stops compression at a fixed location so that a set distance is achieved from the aperture 136 and the target region 140; and so that a repeatable image size is attained.

Illumination

As noted, in a preferred embodiment, the camera system of this invention includes a light source that illuminates the target area. In a specific embodiment the sleeve 132 can be made to rotate so that images are gathered from difficult locations in the mouth. Preferably, the light source is tied to fiber optics which rotate with the sleeve so that regardless of sleeve position the source-to-target area remains approximately fixed. In another aspect, the camera includes optics, such as image collection optics and/or an entrance window. In an embodiment including this feature, the camera optics is tied to fiber optics, so that images are captured effectively regardless of the position of the sleeve.

In another aspect, the sleeve used with the dental camera system of the present invention incorporates imaging optics which relay the tooth image through a Lyot stop, to prevent passage of unwanted light energy to the camera detectors. In a specific embodiment, the sleeve incorporates baffling—such as "two-bounce" optical stray light baffling—to reduce or substantially eliminate stray light from external sources to the desired tooth image area.

Figure 7:
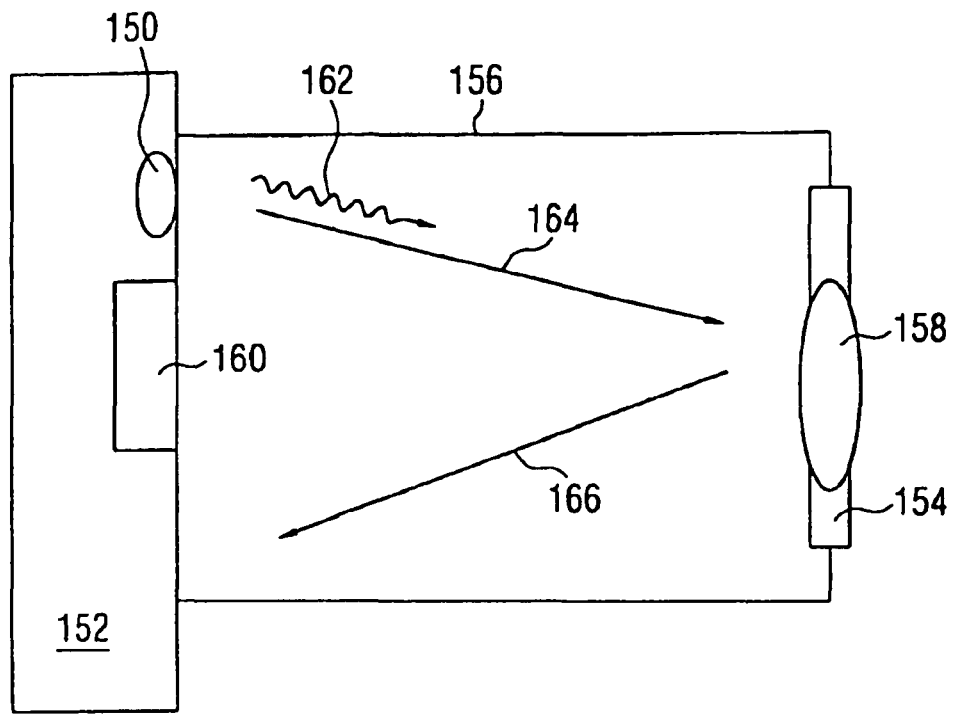
FIG. 7 illustrates a source-to-tooth illumination, for improved image capturing in accord with one embodiment of the invention.

FIG. 7 shows illumination arrangement wherein the source 150 of the illuminating wand 152 (connected to the solid state camera, not shown) is angled from the target area 154. As shown, the sleeve 156 connected to the wand 152 is arranged adjacent to a patient's tooth 158, so that digital images can be taken of the tooth 158 (according to the practices discussed herein) through the wand's optical entrance aperture 160.

For purposes of illustration, FIG. 7 also shows how light 162 emitting from the source 150 travels in a generally specular direction 164, reflecting off the tooth 158 into a direction 166 that is away from the aperture 160. Those skilled in the art will appreciate that scattering does occur off the tooth 158 and into the aperture 160, but that the arrangement eliminates some unwanted reflections into the aperture. Light captured through the aperture 160 is relayed by optics (e.g., fibers and/or relay lenses) to the camera's focal plane (not shown) to generate digital images of the tooth 158.

Figure 8:
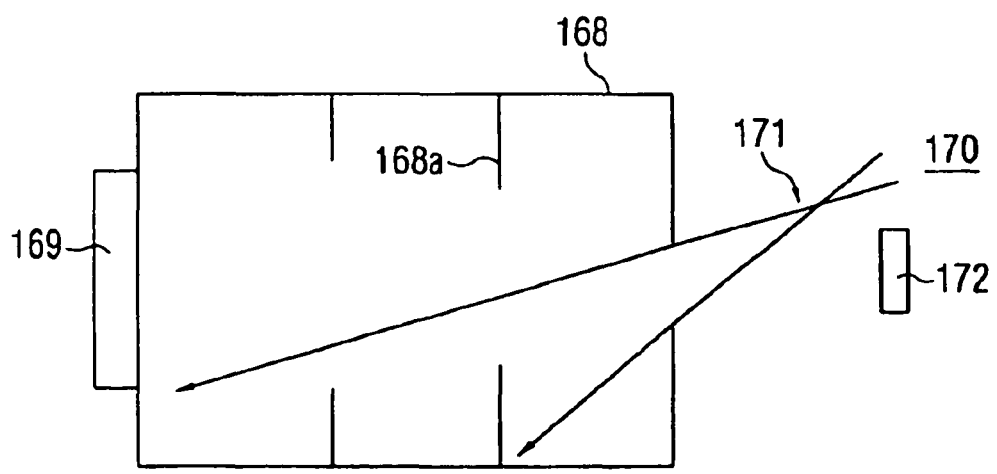
FIG. 8 illustrates baffling and stray-light rejection within a sleeve in a specific embodiment of the invention.

FIG. 8 shows another embodiment of a sleeve 168 constructed according to the invention to reduce passage of light 171 into the wand's entrance aperture 169 from sources 170 away from the target object (e.g., the tooth 172). The sleeve 168 is especially useful in imaging the tooth 172 without adjacent proximity to the sleeve 168, as illustrated in FIG. 8. The sleeve 168 includes baffles 168a known in the art, which require at least one "bounce" and preferably two bounces of the light 171 prior to gaining access to the entrance aperture 169, thereby significantly attenuating "out of field" sources 170 (i.e., those unwanted sources which might influence the color measure, e.g., room lighting). For simplicity, in this illustration the wand and solid state camera are not shown. Baffles 168a can be placed within other sleeves shown herein to improve out-of-field stray light rejection.

As noted above, in order to ensure high-quality images which do not depend on the specific lightning conditions at the time the pictures are taken, in accordance with this invention it is important to minimize the influence of such factors. Accordingly, in another specific embodiment, the sleeve used in the dental camera system of this invention includes a reference sample disposed at the end of the sleeve, near the target area, so that: (a) color comparison information can be obtained; and/or (b) the camera has sufficient reflective surfaces from which to effectively trigger the camera's auto-brightness and/or auto-color features. Specifically, as to feature (b), certain cameras available on the market include electronics and software which automatically adjust brightness and/or color in a digital image. Preferably, in this embodiment such features are disabled. In the event they are operating, however, the reference sample is sized so that a sufficient reflection area is generated at the end of the sleeve, whereby the camera can operate to capture good color images. By way of example, as to feature (b) above, the sample should be sized so that RGB values vary in a controlled or calibrated manner throughout the reasonable tooth shade reflections (e.g., throughout all VITA Shades).

As to feature (a) above, one preferred embodiment utilizes the reference sample to obtain a color reference used to reduce variations in the digital image. "Color" is based on "reflection"—that is, what the camera sees at the target area is based on reflection of whatever source illuminates the target. With the sleeve used in a preferred embodiment, the source is limited to the camera's illuminating source, thereby eliminating other sources and color variations that are not controllable (e.g., the ambient lighting in a building). It is well known that a black body absorbs visible light; and a white object reflects the light. In one embodiment, therefore, the reference sample is as white as possible so that it exhibits very little color (and particularly, the sample reflects light equally in the visible light range from between about 400 nm to 800 nm). When using a white reference sample in accordance with this embodiment of the invention, the following process occurs:

1) Compute average RGB values (and/or other image variables such as hue) for several or all pixels imaged of the reference sample. This computed average is referred to as REF RGB.
2) For each digital image (i.e., for both REFERENCE IMAGES and REAL IMAGES), subtract REF RGB from RGB pixel values for that image. Keep track of the sign (i.e., positive or negative) of the result. The result is referred to as "REF RELATIVE RGB" (i.e., image RGB-REF RGB).
3) Utilize a correlation algorithm, such as described above, (i.e., for the CMN) on REF RELATIVE RGBs as opposed to absolute RGB values (for the pseudo-pixels). Note that when the RSS (i.e., subtract and square) of the CMN algorithm is computed, the sign of the REF RELATIVE RGB matters. For example, if the REFERENCE IMAGE RGB is −0.1, −0.5, −0.6, and the REAL IMAGE RGB is 0.1, 0.7, 0.9, then this REAL IMAGE has quite a bit more color difference (compared to the REF IMAGE, which is the important quantity) than, e.g., a REAL IMAGE with −0.05, 0.2, 0.1. Afterwards, the square of the RSS destroys the sign importance.

The reference sample compensation algorithm described above is used in a specific embodiment to compensate for certain variations. Thus, the auto-brightness feature of certain cameras changes the color of the light emitted from the camera (this is sometimes referred to in the art as the color temperature). Unfortunately, the emitted RGB is not known except for the reference sample, which reflects the source light back to the camera detectors. A good reference sample will thus reflect nearly all colors equally. Since one is interested in differences between REAL IMAGES and REFERENCE IMAGES, the real concern involves differences and not absolute colors.

The reference sample compensation thus also compensates for image acquisition changes which occur over time. For example, the source may emit more or less light, over time, even over several minutes or hours; and it would be desirable to eliminate such variations to increase the sensitivity to color comparisons. The passage of time during an image acquisition sequence only adds to the variability in the measurement: the source color temperature may change, the detector sensitivity or gain may change, etc. With the above reference sample adjustment, if for example one has a perfect white tooth, then its REF RELATIVE RGB is 0,0,0. Assuming that a tooth shade exists that was also perfectly white, it would have a REF RELATIVE RGB of 0,0,0—creating a match.

In another embodiment, the white reference is integrated to find REF RGB, per frame. REF RGB is then subtracted from each pixel RGB in the image (or the other way, i.e., image RGB subtracted from REF RGB, as long as consistent throughout every measurement). In another embodiment, REF RGB is subtracted from pseudo-pixels; but preferably REF RGB is subtracted from real pixel RGBs.

In another embodiment, the sleeve used with the dental camera system of the present invention is formed in the following way. At the end of the sleeve, a central aperture exists preferably in the middle of the target area (e.g., an object such as a tooth or shade is placed at the aperture). Surrounding the central aperture is a black border, to provide high contrast at the edges of the target object. A target object such as a tooth is thus readily defined and discerned within the black border. The aperture also fixes the size of the image for the tooth or tooth shade. Some or all of the remaining area at the end of the sleeve (captured by the camera detectors) in the target area is a white reference sample.

The amount of white reference sample in the target area can be chosen experimentally. By way of example, the average mid point in the auto-brightness (if operating) is obtained so that on average REF RGB changes little. The size of the white sample in the target area is adjusted in area until REF RGB is minimized for all shade values, e.g., A1-A4, B1-B4 and so on. With more black in the image due to less reference sample area, the auto brightness control on the camera (if applicable) adjusts to higher gain to 'balance' the intensity of the image, causing the reference and sample parts to saturate in the red and green.

As noted above, in a specific embodiment, the walls of the sleeve are selected mat black to eliminate reflections, but the facing plate containing the target area is bright to force the camera gain downwards, out of non-linear color operability. In this embodiment preferably the camera's auto features are turned off (and at least any white balance is set to manual). In one specific embodiment, the reference sample is made of a light colored felt material. In alternative embodiments, the sleeve walls are made of a felt material. In these embodiments, the felt material has elements which extend away from the material producing more of a lambertian surface. Such surfaces are preferred as they reduce unwanted specular reflections. Also, the sample reference produces an excellent image when it is not specular. Alternatively, a black velour paper can be used in the sleeve, such as by J L Hammett Co.

Figure 10:
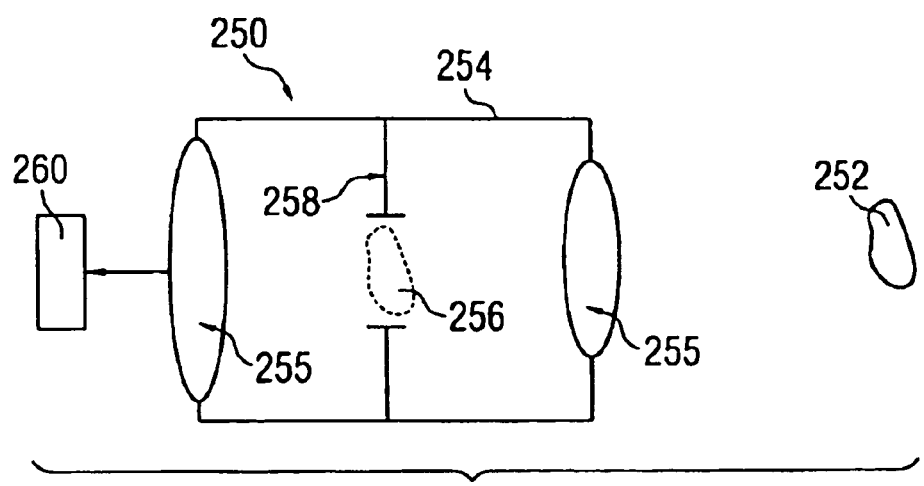
FIG. 10 illustrates a non-contact tooth imaging system, with stray light rejection, constructed according to a specific embodiment of the invention.

FIG. 10 illustrates a non-contact re-imaging system 250 used in accordance with another embodiment of the present invention to image a target tooth 252 without contact between the tooth 252 and a sleeve 254. Optics 255 reimage the tooth 252 internal to the sleeve 254, at internal image 256, and a Lyot stop 258 is used to reduce unwanted stray light entering the aperture 260 to the camera (not shown).

Figure 11:
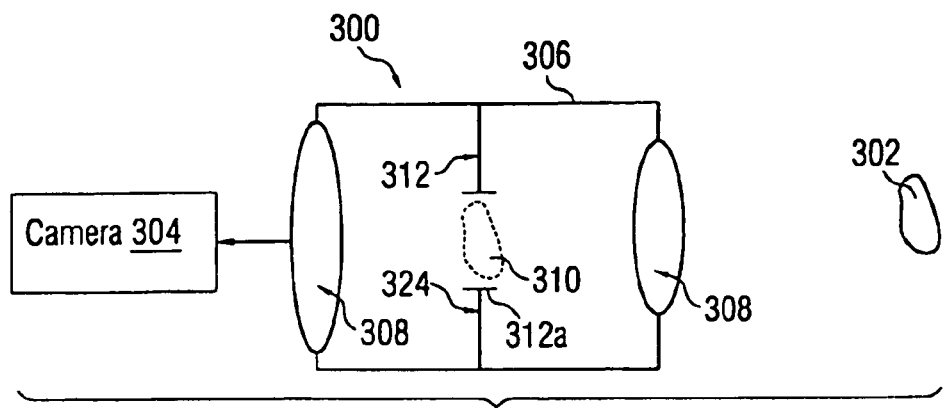
FIG. 11 illustrates another embodiment of a non-contact tooth imaging system in accordance with the present invention.
Figure 12:
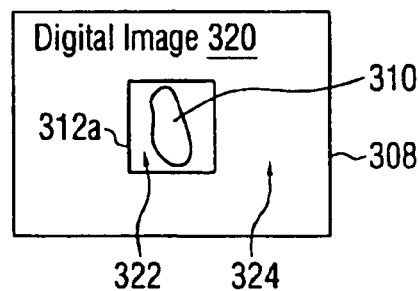
FIG. 12 illustrates a digital image of a tooth.

FIG. 11 illustrates a non-contact re-imaging system 300 used to image a target tooth 302 to a digital camera 304, and without contact between the tooth 302 and the system 300 or camera 304. Although this reimaging system 300 can be made in several forms, in one embodiment the system 300 includes a sleeve 306 that permits hand-held manipulation into a patient's mouth to capture the digital image of the tooth 302. By way of example, optics 308 reimage the tooth 302 internal to the sleeve 306, at internal image 310, and a stop 312 is used for color referencing in analyzing the tooth color. Stop 312 forms an aperture defined by edge 312a. FIG. 12 illustrates one digital image 320, as taken by camera 304, of the tooth 302 and the inside view of stop 312. The region 322 defines that region inside the patient's mouth that is not the patient's tooth 310. Region 324 consists of a color reference which is used as described herein to relate and compare to color pixels of the digital image of the tooth image 310, so as to better define tooth color. Region 324 is preferably the inside of stop 312.

Figure 13:
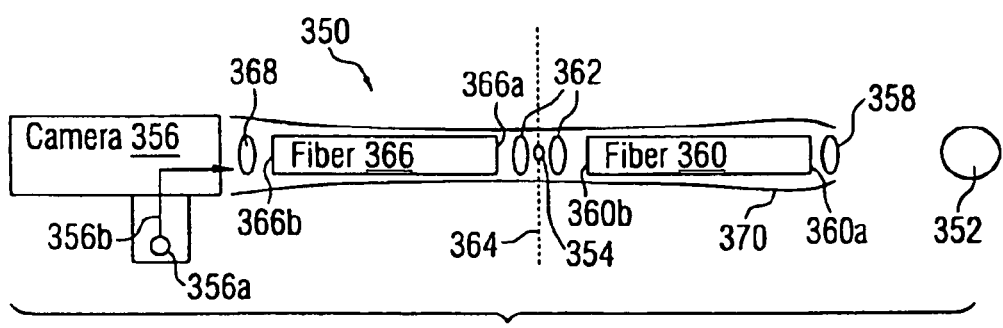
FIG. 13 illustrates a system for reimaging a tooth.

Those skilled in the art will appreciate that a reimaging system such as in FIG. 11 can be made in several ways. By way of example, system 350 of FIG. 13 shows one system of the invention to reimage a tooth 352 to an internal image 354 for reimaging into a digital camera 356. As above, camera 356 takes SNAPSHOTs of the tooth 352, for color analysis. Optical element 358 images the tooth into optical fiber bundle 360, which relays the image from one side 360a to the other side 360b of the bundle 360, as known in the art. Optical elements 362 provide for reimaging to form the internal image 354 at the stop 364. As above, the stop 364 has a reference color disposed thereon, facing camera 356, so that a reference color image is attained such as in FIG. 12. Fiber optic bundle 366 relays the image 354 from side 366a to 366b, and exit optics 368 provides for relaying the tooth image to the camera 356. One convenient feature of system 350 is that fibers 366, 360 can be flexible; and a sleeve 370 can support these elements to provide a hand-held wand that can be inserted into a patient's mouth to acquire the image. Camera 356 can provide its own light source 356a which generates light 356b back along the optical path taken by tooth image 354. The advantage of this is that source 356a can be carefully selected for its color characteristics to facilitate tooth color detection; and further light 356b can illuminate stop 364 inside the sleeve or wand 370 so that the camera 356 can detect and compare its color to the tooth's color image 354.

Tooth Restorative Processing

Figure 14:
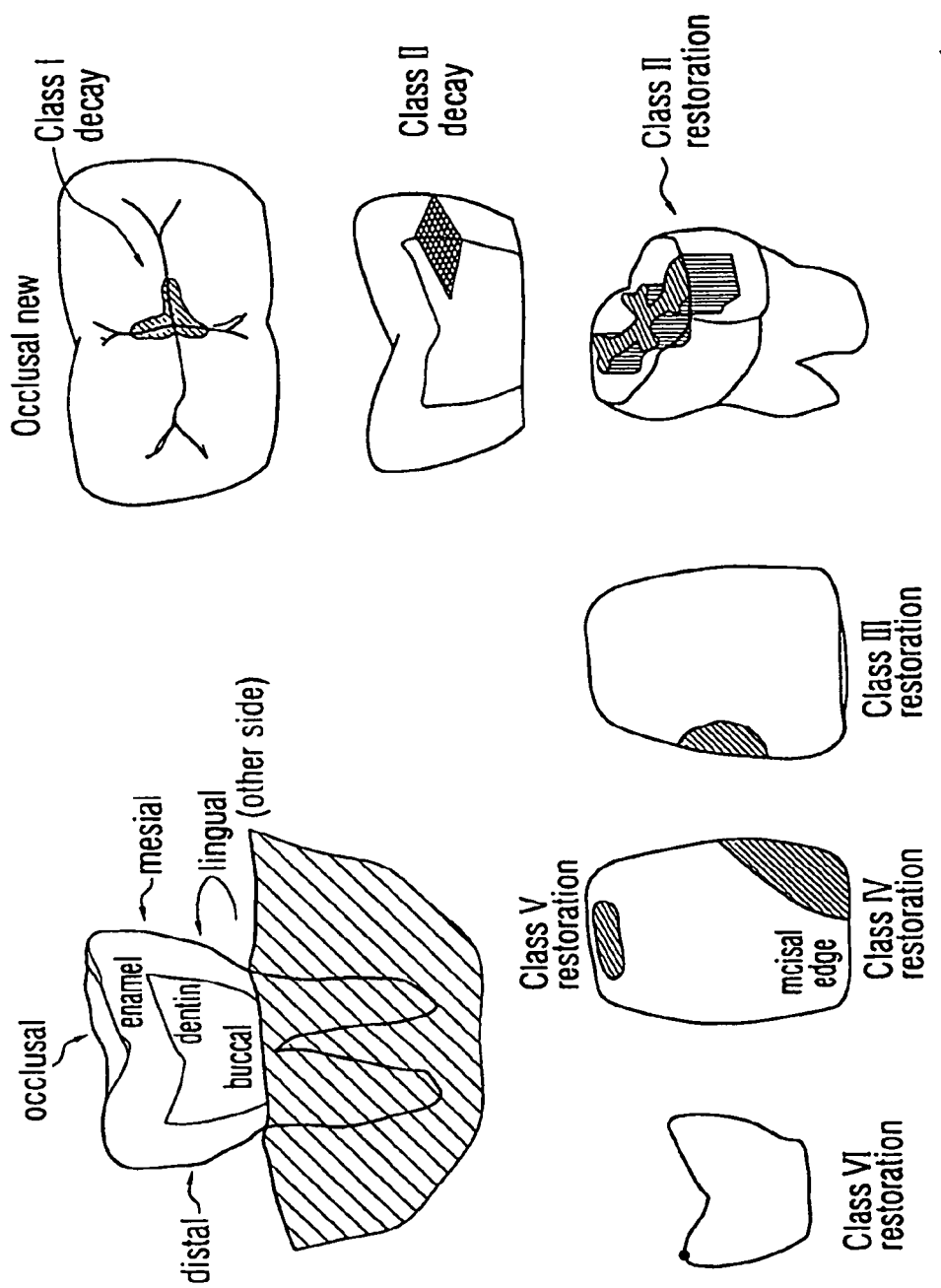
FIG. 14 illustrates various tooth decay patterns and restorations that can be addressed in accordance with the present invention.

FIG. 14 shows certain tooth restorations and decays, which illustrations can help understand more fully aspects of the invention discussed above. A healthy tooth, free from any decay with no current restoration ("restoration" is any part of a tooth that is replaced with a material that allows the tooth to remain in the mouth as a functioning and whole structure) is referred to as a "virgin" tooth. Despite advances in preventative treatment and services (fluoridated water, fluoride treatments, sealants—which are unfilled resins that are bonded into deep grooves of posterior or back teeth to prevent decay in those areas), 50% of American children by age 12 have occlusal decay (decay in the top, or biting surface) in permanent molars which erupted or came into their mouths at age 6.

Typical progression of decay in a tooth is as follows: Following C. V. Black's classifications, a tooth can require a restoration in the following positions:

CLASS 1—occlusal area, that is, within only the top or biting surface of the tooth, usually beginning in the groove or crevice. This term is used only for posterior (back) teeth, i.e., molars and premolars.

CLASS 2—area made up of occlusal and one or more sides of the tooth, either mesial (wall towards front) and/or distal (wall towards back) and or buccal (wall towards cheek) and or lingual (wall towards tongue) so that a class 2 restoration may be termed "MO" (mesial-occlusal), "MOD", "OB", etc.

CLASS 3—area of an anterior, or front, tooth involving only an interproximal wall, that is mesial or distal, areas that face neighboring teeth.

CLASS 4—area of an anterior tooth involving the incisal (bottom) edge and an interproximal wall.

CLASS 5—area of any tooth on only the buccal or lingual wall.

CLASS 6—area of a tooth involving the cusp tip (cusp being the highest point of the tooth, like the mountain peak; this would apply to canines, premolars, and molars).

Once decay is detected, through clinical examination, radiographs, etc., the decayed portion of the tooth needs to be removed. This is achieved through the use of a handpiece (drill). Once excavation of decay is complete, the remaining tooth structure is evaluated for restoration possibilities. A "filling" is placed if 50% or more of the tooth remains, with the stress-bearing areas of the tooth remaining intact (such as cusps and walls of the tooth which are active in biting and chewing process). If these areas of the tooth are compromised, a laboratory-processed restoration is required.

Consider a specific example, in which it is assumed that the tooth needs a restoration, which will be placed right in the office, say a MO on a molar. The choice of materials is made, which could be either amalgam (silver, not done much any more), or composite or ceromer, which are tooth-colored direct materials (Matrix of ground plastic and/or glass in a bis-GMA resin). A shade needs to be selected for the material, such as described herein in accord with the invention. The tooth is cleaned and isolated from saliva and blood by use of cotton rolls, matrix bands, possibly a rubber dam. The tooth surface is etched with a cleanser (typically 37% hydrophosphuric acid), rinsed, and treated with an adhesive, which is bonded to the tooth by use of a curing light—a light with a wand attachment that is about 11-13 cm in width and emits a light in the range of 400-500 nanometers. The material is then placed into the cavity by hand instruments or via dispensing through a carpule/cartridge system in a syringe. The material is somewhat condensed into place at 2-3 mm intervals, and light cured in between. Upon final filling, the restoration is polished and contoured using finishing burs (tips) on the handpiece (drill).

If the tooth requires a lab fabricated restoration, such as an inlay, onlay or crown, further steps need to be taken (Inlay being a Class 2 restoration NOT including cusps, onlay being a Class 2 restoration including cusps, crown being full, or total coverage of the tooth). The tooth is shaped to make the final shape not have any undercuts, with walls as parallel as possible for retention purposes.

Then an impression, or mold is taken of the tooth, which is in a material that remains accurate despite temperature changes, moisture, pouring stone into the mold and removing it several times. An impression of the opposite arch of teeth, or opposing arch, is taken also so that the technician can articulate, or put together the two arches and simulate the patient's mouth or bite. A registration of such a bite can be taken also and sent with the case. So that the things sent to the lab for such a case are: impression of the tooth to be restored and adjacent teeth, model or impression of opposing teeth, and possibly a bite registration.

Those skilled in the art should appreciate that the invention to determine the appropriate color shades of the tooth as illustrated in FIG. 14 can be accomplished by the methods herein, and/or by systems disclosed in the several figures. Using a wand of the invention, furthermore, various teeth (as in FIG. 14) can be acquired for digital evaluation. In accord with the invention, digital files of patients' teeth can be stored in memory of computer 14, FIG. 1, for a permanent record. A patient can then be evaluated over time for color changes.

Multifaceted Tooth Restorative Processing

In dental restorative cases, the general dentist is the master planner, or gatekeeper of all phases of the patient's treatment. In some more complex cases, the general dentist still performs this function even if the dentist does not perform the dental restoration. For example, consider an adult patient that is suffering from malocclusion or misalignment of teeth. Nearly everyone has some degree of malocclusion, although it is not usually serious enough to require treatment, however, some patients may require multidisciplinary treatment. Most instances of malocclusion are discovered by general dentists during a routine examination. The general dentist usually refers the patient to an orthodontist for further diagnosis and treatment. In some instances extraction of one or more teeth may be required if overcrowding is part of the problem. This is usually performed by an oral surgeon but may be performed by a general dentist as well. In some instances an oral surgeon may place implants to serve as locator attachments for removable partial dentures that are designed by the general dentist, a prosthodontic lab practitioner or technical sales rep. The general dentist may also adjust, reshape, bond, or cap any remaining rough or irregular teeth. Thus, the treatment plan from start to finish can involve a general dentist, an orthodontist, an oral surgeon, a removable prosthodontic lab technician, a technical sales rep, the patient, or a combination thereof. This type of treatment plan can require considerable amount of information exchange between the practitioners involved, and consequently can be time consuming, inefficient, and troublesome. As further discussed below, a computer-based dental restoration system can provide a more smooth implementation of the treatment plan if some or all the practitioners involved use the system to examine a video, an X-ray, or images of the patient's mouth together simultaneously, or substantially simultaneously, in disparate locations. The system can provide further advantages if some or all the practitioners use the system to directly communicate with each other in addition to using the system to examine images of the patient's mouth.

The provision of a dental restorative network for communication between a lab and dentist also facilitates participation by other users in an expanded network, which would allow multiple users to simultaneously access the same case and have a "conference" in real time to discuss treatment possibilities, troubleshoot the case, and have interdisciplinary discussion of phases of treatment for a patient.

In a preferred embodiment, the computer-based dental restoration system includes a network server having a database for storing digital representations, and a communications network providing access to the network server and facilitating direct communication at least between a dentist and a practitioner. The system further includes one or more computers for accessing digital representations over the communication network. The one or more computers can display the digital representations in a convenient format. Preferably, the practitioner includes one or more of a dentist, a dental specialist, a dental restoration manufacturer, an authorized user, or a combination thereof. Illustratively, the dentist and or a practitioner can set up a Web site for a patient by storing the patient's digital representations onto the database of the server. The storing of patient's digital representations is preferably performed using a loading application for loading the digital representation into the database.

Advantageously, the digital representations include one or more of a patient's dental record or aspects thereof, an x-ray of a patient's tooth, a digital image of a patient's tooth, a video image of a patient's tooth, or a preliminary dental treatment plan. The digital representations preferably further includes a digital impression which is a three dimensional model of the treatment area. Preferably, an intraoral scanner is used to form this three dimensional geometry. In some embodiments a dental cast can be used to obtain a digital impression. The digital impression can provide detailed model of the treatment area. A Computer Aided Design (CAD) machine can use the detailed model to design, for example, a fixed prosthodontics. This design can subsequently be applied by a Computer Aided Mill (CAM) machine in the fabrication of the fixed prosthodontics. In another application, the digital model can be used in a simulation of a patient's course of treatment, where the dentist, practitioners, and possibly the patient can observe various stages of the treatment on a computer monitor. The simulation can be visually displayed for example, by a computer monitor, a television, a holographic display, or other devices known in the art. The simulation can be displayed on devices capable of displaying 3-D images or stereo images, from a plurality of view points, and plurality of projection types. Preferably, the dentist and practitioners can attach text, voice, video, and files to a particular digital representations or portions thereof. In yet another application, multiple forms of digital representation can be compiled into a multi-layer object for visualization and analysis of a treatment area. For example, an X-ray of a treatment area can be projected on to a cross-section of a digital impression of the same area.

The Web site can control access using a user name, an identification number, a password, and possibly other means to protect patient's privacy and to comply with Health Insurance Portability and Accountability Act (HIPPA). As further discussed below, the Web site also can include a number of individual demarcated sections or Web pages that allow or deny access as needed (see FIG. 18). For example, the dentist might be allowed access to all information for all patients, whereas the another practitioner or a guest practitioner might be permitted access to a certain portion of a patient's record while providing consultation to the dentist. Once the Web site is properly configured, the dentist for example, may invite other practitioners to join him/her in a conference to discuss a patient's treatment plan. The dentist and practitioners (i.e., participants) preferably access the database via a client application running in one or more computers. Preferably, the client application includes a Web browser that can connect to the Web server for access to the database. The participants can also conference together, preferably via establishment of direct communication, using for example a HIPPA compliant client-server instant messaging application, such as, Mirador instant Messenger or other instant text and voice messaging tools known in the art. The participants develop an initial treatment plan, or meet later in the treatment to access progress, or to troubleshoot problems that may occur. Preferably, the one or more computers provides the participants simultaneous access to at least one of the digital representations.

Figure 19:
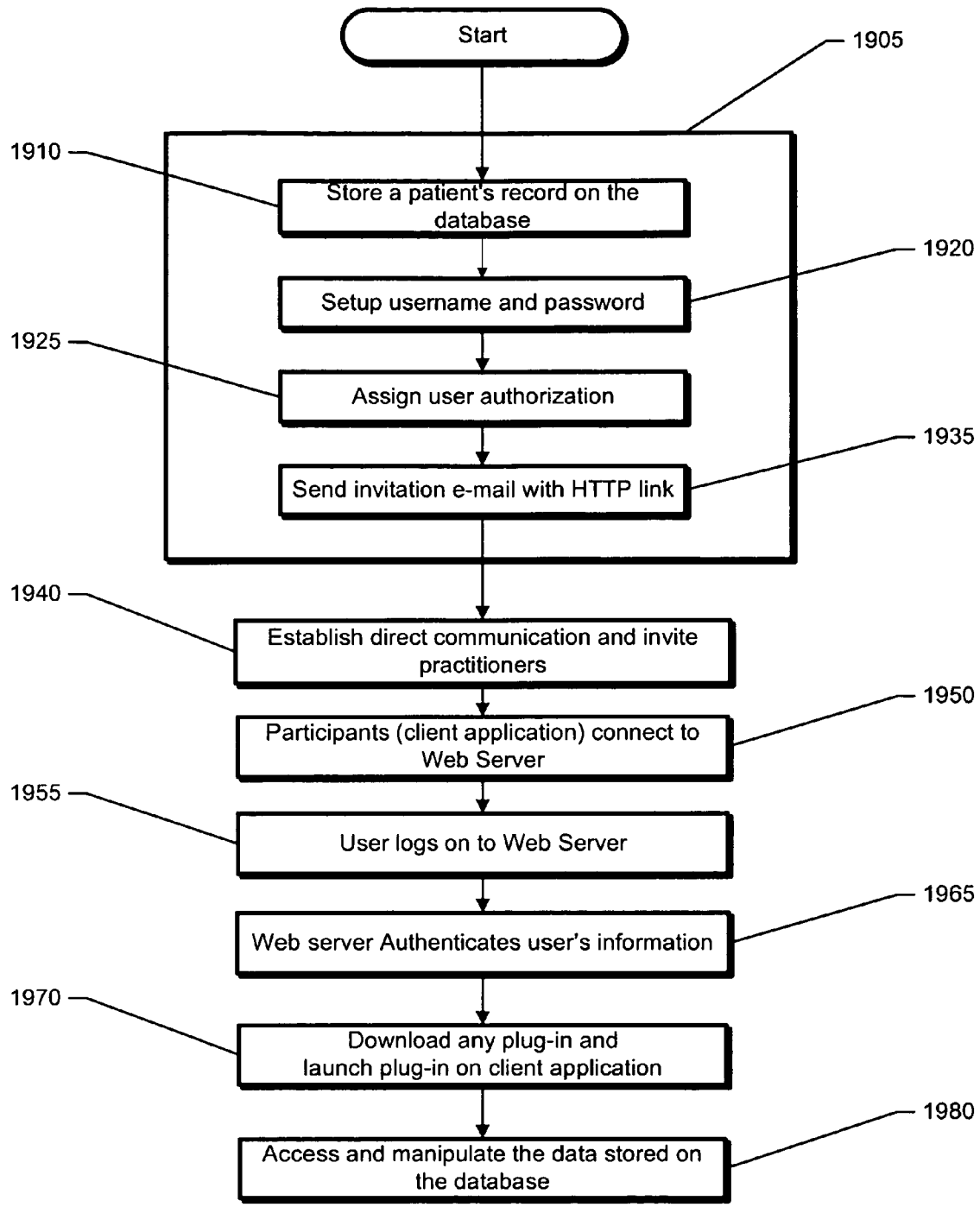
FIG. 19 is a flow diagram depicting operational process of the interactive network system of the invention.

FIG. 19 illustrates in a block-diagram form the operational process of the computer-based interactive network system in a preferred embodiment. In operation, the dentist stores a patient's record 1910 on the database using a loading application 1905. The patient's records can include, for example, an X-ray, images, a digital impression, and a treatment plan. The loading application 1905 may allow the dentist to send e-mails 1935, containing the HTTP link to the site storing the patient's record, inviting other practitioners to join in. In some instances, the dentist might extend a conference invitation to other practitioners using an instant messaging application 1940. Upon connection to the server 1950, the participants can be promoted to login 1955 using a user name and a password previously assigned 1920 by the dentist, the server can then authenticate 1965 the user and provide access to the patient's record according to privileges previously set 1925 by the dentist. In certain instances, the client application running on the participant's computers can download a plug-in before launching an application 1970. The participants can then interactively access, operate or manipulate the data stored on the database 1980. Preferably, the participants can have simultaneous access to the database while directly communicating with each other, for example, using an instant messenger application 1940.

In another embodiment, the computer-based dental restoration system can communicate information between the dentist and practitioners via e-mail. In this case, at least one of the one or more computers, the server, or both include an application that provides access to the database via e-mail. For example, the dentist can request the application to send e-mails, via the communication network, containing a set of digital representations of a patient to one or more practitioners. The practitioners can then be notified by the application upon reception of the e-mail from the dentist.

As another illustration of the present invention consider the fabrication of fix prosthodontics. Traditionally, if a patient needs fixed prosthodontics, such as a crown, the dentist would be required to obtain a full or partial cast from the patient's mouth (teeth) and send the cast along with the preparation instructions to a laboratory practitioner for design and construction. Often, this process would be followed by further communication between the doctor and the laboratory practitioner to resolve any questions that the laboratory practitioner may have, or the laboratory practitioner informing the doctor that additional modification or steps would be required by him/her to ensure proper fitting. For example, in some cases the dentist may be required to take a new impression due to ineffectiveness of the original impression or perform further tooth reduction to allow for clearance, which would mean more chair time. Generally, the entire process for a crown may take several weeks depending on the complexity of the case.

Advantageously, digital representations allow for communication of detailed information regarding patients to various practitioners for consultation and development of treatment plan. A digital impression from a patient's mouth or teeth can provide the necessary information for a practitioner in a dental laboratory to build a prosthesis for the patient based on the instructions from a dentist. In accordance with the present invention, a dentist can, for example, use an intraoral scanner to obtain a digital impression of the mouth or part of the mouth requiring treatment. The dentist reviews the digital impression on the chairside screen at the same time a validation program can be run to determine the effectiveness of the impression. If the dentist has a CAD/CAM machine in the office, then the dentist can choose to design the crown himself/herself, alternatively, the dentist can choose to utilize the talent of a prosthodontic lab practitioner for this work.

If the decision is to let the prosthodontic lab practitioner do the design, then the digital impression data can be sent, preferably by Internet, to the design lab, with the patient still in the chair. The prosthodontic lab practitioner receives the data and designs the case by operating on the data received from the dentist, and sends the designed crown back to the dentist for his/her review and acceptance. Generally, the time required for data exchange and design of the crown can be of order of minutes, for example 10 minutes, and can cost the dentist less $100, for example $45 in the 2006 valuation. The dentist upon receiving the designed crown can review it, and accepts it or reject it, with the patient in the chair. If acceptable, the dentist can choose the design lab to mill the crown with possibly additional directives, for example, more translucency must be added to the crown to match the other teeth. The dentist can choose to mill chairside if the crown as designed can match using the chairside blocks without other characterization. In the former case, the dentist can deliver the crown to the patient in just a few days; in the latter case, a single office visit can afford the patient a new crown.

In another preferred embodiment, the computer-based dental restoration system includes a network server having a database for storing information about materials, procedures, preparations concerning dental restoration prostheses, and digital representations. The system further includes a communication network providing real-time access to the network server, and at least a dentist and a practitioner. The computer-based dental restoration system also comprises one or more computers for accessing the database over the communications network and displaying the information in a humanly readable format. Preferably, the communications network is configured to enable the dentist to communicate a prostheses specification, consult with the practitioner, obtain cost and viability options for presentation to a patient, and place an order with the practitioner, wherein elapsed time for the whole process is less than four hours. More preferably, the elapsed time is less than one hour.

Miscellaneous Aspects

Although the VITA™ Shade guide is often discussed herein, it should be apparent that other shade guides and porcelains can be stored as REFERENCE IMAGES and compared to REAL IMAGES in alternative embodiments of this invention. Computer memory can store a large number of images, even from different manufacturers, so as to provide the optimum color fit to a patient's tooth. By way of example, IVOCLAR has one suitable shade guide, as well as various materials of porcelains, ceromers, polymers, and others. In accord with the invention, a database can store REFERENCE IMAGES for match correlation to REAL IMAGES. Alternatively, in one aspect, the invention performs a conversion to other manufacturer shades and or porcelains so that alternative laboratories can be used without undue concern for manufacturer alliance. Specifically, in accord with one aspect of the invention, a conversion between known shade guides is provided for increased lab selectivity. It will be appreciated that the conversion of digital images involves mapping from one set of color coordinates to another, which procedure is well known in the art and need not be considered in further detail.

As described, one major problem due to auto brightness is that if there is not enough light material in the image, the auto brightness turns the gain up too high, and the R and G values saturate in the sample. By adding sufficient light colored reference area, the balance of light to dark is better, but the reference can saturate in places. This can be compensated some by using an end plate at the end of the sleeve that will be all white but with the black border round the sample aperture. A reference color area can be included in one corner so that the camera adjusts brightness for the constant white area leaving the reference and sample somewhere in the middle of the operable RGB ranges.

In still another aspect, instead of subtracting the RGB from the reference sample, an average of the reference sample is used. Specifically, over the range of images taken, an average REF RGB (denoted "AVE REF RGB") is determined for the reference sample. For each individual image, the difference is calculated between the REF RGB and the AVE REF RGB. This delta RGB is then added to the image RGB to correct for any compensation in the camera. Thus if the image is brighter than the average image, the difference is subtracted from the sample values and vice versa.

In still another aspect, the reference sleeve has an end plate which contains all tooth shades for a given manufacturer (so that one sleeve is used for a particular manufacturer). Any image therefore acquires the sample tooth as well as all the tooth shades; and image processing commences on the one digital image. This is advantageous in that camera color drift is compensated for since all images are taken at the same time.

Figure 15:
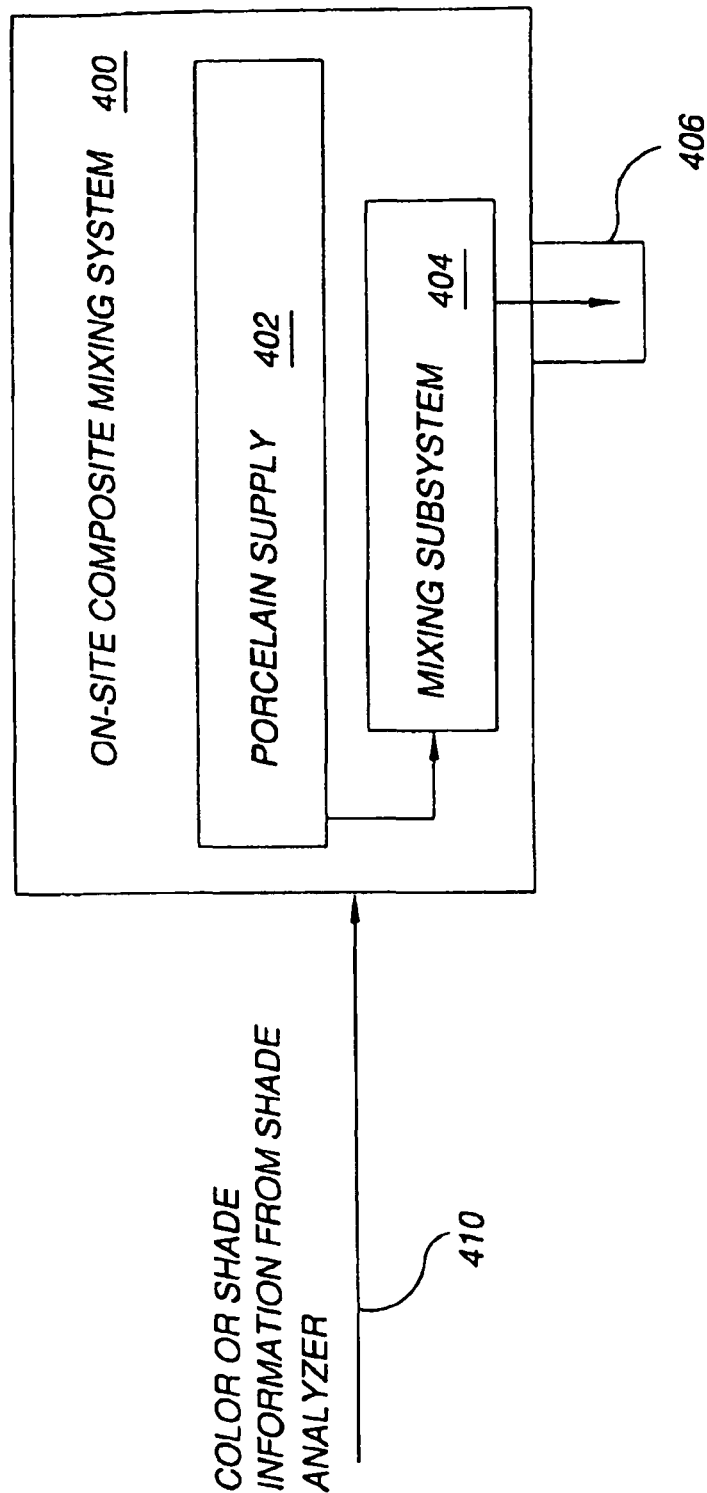
FIG. 15 is a schematic representation of the interactive network system of the invention.

When determining tooth color, if the shade does not correspond to an existing shade (such as A1, D4), a system 400 is provided as shown in FIG. 15 which will create a recipe for whatever shade the tooth is. Color digital information about the tooth under test is sent to system 400 over a communication line such as the Internet; and system 400 selects porcelain mixtures from supply 402 to be sent and mixed within mixing subsystem 404. Subsystem 404 dispenses the mixture into a capsule 406 for the dentist, which administers the final mixture to the patient's tooth.

The new shade material in carpule 406 is either provided chair-side, or reported to the technician over the Internet 410 (in which case, system 400 can be present at the technician's site). If for example the dentist needs to use a composite material like HELIOMOLAR by Ivoclar, and the desired shade is something between C2 and C3, the system determines the new shade of "C2/C3", mixes component composite materials accordingly, and dispenses to the dentist a premixed carpule/cartridge 406 of material to be used on that patient. Information to be sent to the lab can include a recipe that will instruct the technician as to how to create the new shade using whatever material is selected-porcelain, ceromer, pressed porcelain, etc.

FIG. 16 illustrates in a block-diagram form the configuration of the interactive network system in a preferred embodiment. As shown, this system is implemented as a (preferably website) server 1610, having access to one or more databases 1630 containing information about different aspects of dental restoration. As noted, this information in a preferred embodiment includes materials, procedures and preparation recipes related to various dental restoration prostheses, and may include preparation design, recommended burs to achieve such a preparation, recommended temporization materials, cements that should be used with that given material, instructions on how to use such a cement and where to buy such materials, and others. In addition, database 1630 may contain information about different dental procedures, and in particular answers to commonly asked questions. In yet another embodiment, the database may also contain patient histories, so that a dentist (or a technician) having access to the system can read the patient history regardless of where they are located physically, provided that they have proper authorization to access this information. The database may further be connected to external information source(s) providing input from product manufacturers, market research or others. In accordance with the present invention there is no restriction on the type of database 50 design that can be used.

In operation, users can access the service over a communications network 1620, such as the Internet, using data entry devices, designated 1640 in FIG. 16. Generally, devices 1640 can be implemented as any color-display device capable of communicating over the network 1620. In the preferred embodiment where the network is the Internet, for example, such capability is provided by browsers, as known in the art. Thus, a device 1640 can be a conventional personal computer 14, as illustrated in FIG. 1. In alternative embodiments that do not communicate over the Internet such a device should have a capability to communicate over a communications network, e.g., an intranet, as known in the art.

In a preferred embodiment, the server 1610 is a computer, the type of which may range from a personal computer to a workstation or a larger computer or a network of computers. The choice of a specific computer system is based on known trade-offs, and thus will not be discussed in further detail. In the preferred embodiment, the server is Internet-enabled but it will be appreciated that in alternative embodiments it can support another network, e.g., an intranet. Broadly, the server 1610 comprises a processor 1650 and random access memory (RAM) and read-only memory (ROM), collectively designated 1670. The processor 1650 is adapted to execute instructions in different computer languages and can operate in different operating system environments, such as the PC/Windows™ environment. In a preferred embodiment, the server also has a data formatting device 1660 serving to provide interface with the database(s) 1630. In various embodiments the server can be provided with additional devices (not shown) such as a point-and-click device (like a mouse), keyboard, a monitor and various other devices, which may include, for example a printer 46. Preferably, the server is equipped with means for connecting to external communications media, and may include various connectivity types, such as a LAN connection.

It will be appreciated that using the system shown in FIG. 16, different users 1640 can access information stored at the network server (or to which the server has access). It will also be appreciated that the system would enable direct communication between users, such as on-line communication between a dentist and a dental restoration laboratory, where the two sides can simultaneously have access to a patient record, an image of tooth in need for restoration or others. Naturally, if desired, such communications can be established over dedicated lines although in accordance with this invention it is desirable to use open systems, such as the Internet because of the flexibility they provide. Further, while they are shown separate for illustration purposes, it should be apparent that the server 1610 can physically be located at the dentist's (or laboratory) office.

Figure 17:
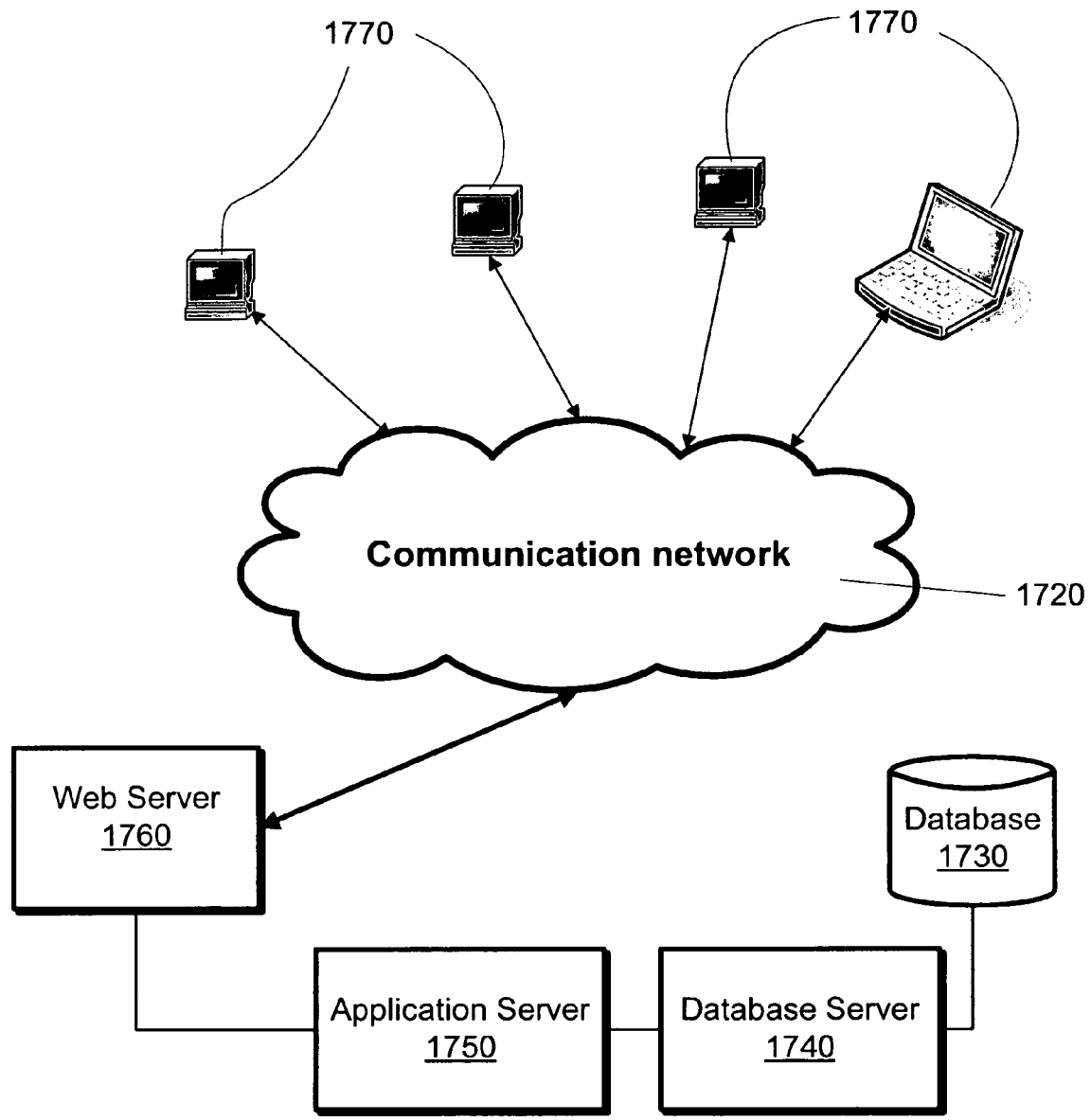
FIG. 17 illustrates an embodiment of Web application components of the interactive network system of the invention.

The Web site can include one or more Web applications, each providing specific information or functionality to the user. FIG. 17 illustrates a preferred embodiment of the interactive computer-based network system, where clients connect to a server across a communication network to obtain access to a Web application. A general Web application consist of five major components, a Web server 1760, an Application server 1750, a database server 1740, a database 1730, and a Web browser (client) 1770. A Web server 1760 preferably runs specialized Web server 1760 software that supports Hypertext transfer protocol (HTTP) to handle multiple Web requests and is responsible for user authentication in case of intranet and extranet applications. An application server 1750 generally performs most of the application processing logic and is also in charge of maintaining the state management and session control logic that are required for an online system. Preferably, the database server 1740 hosts Database Management System (DBMS) and provides data access and management capabilities. In a typical session, the Web server 1760 processes client requests and sends HyperText Markup Language (HTML) pages back to the client. When needed, a Web server 1760 connects to the application server 1750 or database server 1740 to process the necessary logic or database query and sends the result back to the Web server 1760. This exemplarily arrangement does not mean that there must be an application server 1750 for the Web application, and nor does it imply that the Web server 1760, application server 1750, and database server 1740 cannot all be located on the same machine. The decision on architectural components is shaped by the requirements of the application and the existing and future technology.

Figure 18:
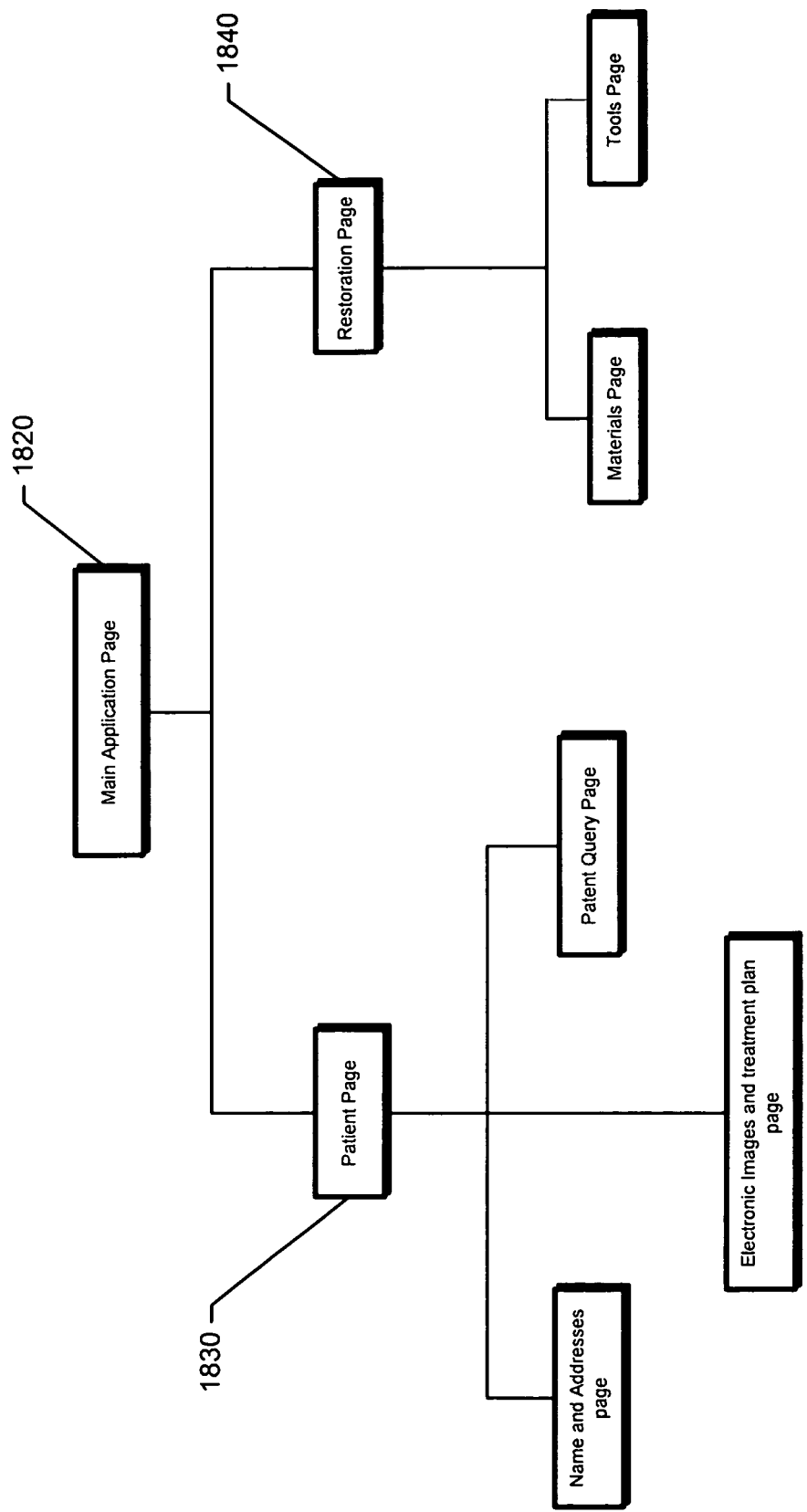
FIG. 18 illustrates an embodiment of Web page layout of the interactive network system of the invention.

Preferably, the Web application is based on individual Web pages, and is divided into clearly demarcated sections, allowing or denying access as needed. Each portion of the application can have its own Web page. As shown in FIG. 18, main application page 1820 is partitioned in to a patient page 1830 that provides access to patient's record, and a restoration page 1840 that provides access to information on dental restoration materials and tools. Each page can include an appropriate user interface for gathering and displaying data to the user, and may also include help right alongside the application's interface and can contain links to almost any other part of the application. Each page can do several functions or just one. Special pages for specific users can be added and accessed based on the user's identity, which can easily be determined and managed, for example, by standard HTTP and Web techniques such as authentication and the use of cookies.

A Web page and its embedded resources can be stored under the Web server 1760 as they delivered (static Web page) or produced dynamically at run-time, upon user request (dynamic Web Page). A static Web Page can, however, be dynamic (active) on client-side through the use of client-side scripting. The client-side scripting are small programs that reside on the Web server 1760 that are download with the Web page to bring interactivity. For example, JavaScrpit, a client-side scripting language, can be employed to facilitate manipulation of images and text, and gathering information from forms.

Dynamic Web Pages are produced dynamically on server-side by a server-side script. Examples of server-side script include Active Server Page (ASP), Common Gateway Interface (CGI) script, Java Active Pages (JSP), Hypertext Preprocessor (PHP). For example, in the case of a Web database access, the Web browser 1770 sends a database request to the Web server 1760. The Web server 1760 passes the request using, for example, CGI to the application server 1750 where the Web-to database middleware may be located. The application server 1750 then uses a database middleware such as Open Database Connectivity (ODBC) to connect to the database. The application server 1750 receives the query result and creates the HTML formatted page and sends the page back to the Web server 1760, the Web server 1760 then sends the page to the browser 1770. In one preferred embodiment, the Web application includes both static and dynamic pages such that to enable online communication between a dentist, a practitioner, and other authorized users, where the participants can simultaneously have access to an image of tooth, patient records or any other appropriate information. Alternative embodiment include cases where the Web application employs static pages only.

While the invention has been described with reference to the preferred embodiments, it will be appreciated by those of ordinary skill in the art that various modifications can be made to the structure, form and operation of the various embodiments of the invention without departing from its spirit and scope, which is defined in the following claims.

For disclosure purposes, non-limiting source code for use with certain aspects of this invention can be found in grandparent U.S. Pat. No. 6,575,751 and is incorporated herein by reference thereto.

What is claimed is:

1. A computer-based dental conferencing and restoration system comprising:
    a network server having a database storing digital representations of dental data for a plurality of patients, the dental data including one or more three-dimensional (3D) digital models and one or more x-ray images of patient treatment, the server enabling conferencing among, and concurrent access to the stored dental data by a plurality of practitioners comprising a dentist, a prosthodontic lab technician, and one or more further dental practitioners, and
    a communications network providing access to the network server and to a plurality of client computers used by the dental practitioners; and
    facilities for computer-assisted-design accessible by the communications network that assist one or both of the dentist and practitioner to design a dental prosthesis suitable to carry out a treatment plan, the design being based, at least in part, on the one or more 3D models of the treatment area;
    wherein the client computers provide or allow accessing of the digital dental data over the communications network, displaying of the digital dental data in a humanly readable format, and conferencing among the plurality of practitioners to discuss the stored dental data in real time in order to communicate and discuss prosthesis specifications, cost and viability options for presentation to a patient, and order placement for the prosthesis and determine an appropriate treatment plan for the patient based on the dental data; and
    wherein the network server provides the plurality of practitioners with simultaneous access to the stored dental data, with each practicioner participating in the conferencing by accessing the stored dental data from a different client computer.

2. The computer-based dental conferencing and restoration system of claim 1 wherein the digital dental data further comprises one or more of a patient's dental record or aspects thereof, a digital image of a patient's tooth, a video image of a patient's tooth, or a preliminary dental treatment plan.

3. The computer-based dental conferencing and restoration system of claim 1 wherein one or more of the digital (3D) models is formed from an impression of the treatment area or formed by the use of an intraoral scanner.

4. The computer-based dental conferencing and restoration system of claim 1 wherein the computers include one or more databases storing information about dental materials, dental procedures, dental tools, and preparation methods for dental restoration, which databases can be accessed by the communications network in real-time.

5. The computer-based dental conferencing and restoration system of claim 1 wherein the practitioner comprises one or more of a dentist, a dental specialist, a prosthetic laboratory, a dental laboratory and a dental restoration manufacturer.

6. The computer-based dental conferencing and restoration system of claim 1 wherein the communications network transfers one or more of voice data, video data, and patient data between a dentist and a practitioner.

7. The computer-based dental conferencing and restoration system of claim 1 wherein the databases further store guidance to assist a dentist in determining an appropriate restorative procedure and to obtain feedback for a patient's specific dental needs.

8. The computer-based dental conferencing and restoration system of claim 1 further comprising facilities for computer-assisted-manufacturing accessible by the communications network that assist one or both of the dentist and practitioner to manufacture a dental prosthesis according to a dental-prosthesis design that is based, at least in part, on the one or more 3D models of the treatment area.

9. The computer-based dental conferencing and restoration system of claim 8 wherein the computer assisted manufacturing facilities are located in one or both of a dentist's office or a dental laboratory.

10. A method for assisting a dental practitioner in the dental restoration of a patient treatment area comprising:
    forming a three-dimensional (3D) model represented in digital form of the treatment area to be restored, the model being formed during a first visit by the patient to a dentist's office;
    developing a preliminary treatment plan including a specification of a dental prosthesis that is based, at least in part, on the 3D digital model of the treatment area;
    storing the 3D digital model and the preliminary treatment plan in a database along with the patient's record;
    conferencing with other practitioners using the system of claim 1 in order to determine whether the preliminary treatment plan is appropriate for the patient based on the dental data; and
    designing the dental prosthesis by means of computer-aided-design facilities that have access to the database to carry out the treatment plan, the design being based, at least in part, on the one or more 3D models of the treatment area.

11. The method of claim 10 wherein the preliminary treatment plan and prosthesis specification are developed during consultation between the dentist's office, a dental laboratory, and a further dental professional, with the database being simultaneously accessible by each party during the consultation by means of the communication network.

12. The method of claim 10 further comprising fabricating the dental prosthesis by means of computer-aided-manufacturing facilities that have access to the database, the prosthesis fabrication being based, at least on part, on the prosthesis design.

13. The method of claim 12 wherein the preliminary treatment plan including a prosthesis specification is presented to the patient during the same first patient visit to the dentist's office and the prosthesis is fabricated in the dentist's office during the same first patient visit to the dentist.

14. The method of claim 10 further comprising simulating the course of treatment, the simulation including images of the stages of treatment.

15. The method of claim 10 wherein the plurality of dental practitioners further comprises appropriate combinations of an orthodontist, an oral surgeon, a dental specialist, a dental restoration manufacturer, a technical sales rep, an authorized user, and the patient.

16. The method of claim 10 wherein the communications network provides communication among appropriate combinations of a dental office, a dental specialist's office, a prosthetic laboratory, a dental laboratory and a dental restoration manufacturer.

17. The computer-based dental conferencing and restoration system of claim 1 wherein the plurality of dental practitioners further comprises appropriate combinations of an orthodontist, an oral surgeon, a dental specialist, a dental restoration manufacturer, a technical sales rep, an authorized user, and the patient.

18. The computer-based dental conferencing and restoration system of claim 1 wherein the digital dental data further comprises one or more of patient dental records or aspects thereof, digital images of patient treatment areas, video images of patient treatment areas, and dental treatment plans.

19. The computer-based dental conferencing and restoration system of claim 1 wherein the digital dental data further comprises, for at least one patient, a simulation of the patient's treatment plan comprising images representing stages of the treatment plan.

20. The computer-based dental conferencing and restoration system of claim 19 wherein the simulation of the patient's treatment plan further comprises 3-D or stereo images viewable on devices capable of displaying such 3-D images or stereo images.

21. The computer-based dental conferencing and restoration system of claim 1 wherein the digital dental data further comprises text, voice, video, and files attached to a particular digital representations.

22. The computer-based dental conferencing and restoration system of claim 1 wherein the digital dental data further comprises, for at least one patient, a multi-layer object for visualization and analysis of a treatment area compiled from multiple forms of digital representation.

23. The computer-based dental conferencing and restoration system of claim 1 wherein the communications network provides communication among appropriate combinations of a dental office, a dental specialist's office, a prosthetic laboratory, a dental laboratory and a dental restoration manufacturer.

* * * * *

UNITED STATES PATENT AND TRADEMARK OFFICE
CERTIFICATE OF CORRECTION

PATENT NO.       : 8,790,118 B2                           Page 1 of 1
APPLICATION NO.  : 11/513273
DATED            : July 29, 2014
INVENTOR(S)      : Lehmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 697 days.

Signed and Sealed this
Twenty-ninth Day of December, 2015

Michelle K. Lee
*Director of the United States Patent and Trademark Office*